US009051582B2

(12) United States Patent
Chatellard et al.

(10) Patent No.: US 9,051,582 B2
(45) Date of Patent: Jun. 9, 2015

(54) EXPRESSION VECTORS COMPRISING THE MCMV IE2 PROMOTER

(75) Inventors: Philippe Chatellard, Lausanne (CH); Markus Imhof, Chexbres (CH)

(73) Assignee: MERCK SERONO SA, Coinsins, Vaud (CH)

( * ) Notice: Subject to any disclaimer, the term of this patent is extended or adjusted under 35 U.S.C. 154(b) by 355 days.

(21) Appl. No.: 12/872,151

(22) Filed: Aug. 31, 2010

(65) Prior Publication Data

US 2011/0008839 A1  Jan. 13, 2011

Related U.S. Application Data

(63) Continuation of application No. 10/548,364, filed as application No. PCT/EP2004/050280 on Mar. 10, 2004, now Pat. No. 7,824,907.

(30) Foreign Application Priority Data

Mar. 11, 2003  (EP) ..................................... 03100617

(51) Int. Cl.
*C12N 15/113* (2010.01)
*C12N 15/11* (2006.01)
*C12N 15/63* (2006.01)
*C12N 15/85* (2006.01)

(52) U.S. Cl.
CPC ....... *C12N 15/85* (2013.01); *C12N 2710/16122* (2013.01); *C12N 2830/205* (2013.01); *C12N 2830/60* (2013.01)

(58) Field of Classification Search
None
See application file for complete search history.

(56) References Cited

U.S. PATENT DOCUMENTS

| 4,963,481 | A | 10/1990 | deVilliers | |
|---|---|---|---|---|
| 4,968,615 | A | 11/1990 | Koszinowski et al. | |
| 7,691,611 | B2 | 4/2010 | Weber et al. | |
| 7,824,907 | B2 * | 11/2010 | Chatellard et al. | 435/320.1 |
| 2002/0065213 | A1 * | 5/2002 | Debs | 514/2 |
| 2003/0166890 | A1 * | 9/2003 | Crombie et al. | 536/23.1 |
| 2004/0076628 | A1 | 4/2004 | Chvatchko et al. | |
| 2004/0161817 | A1 * | 8/2004 | Benton et al. | 435/69.1 |
| 2007/0037734 | A1 | 2/2007 | Rossi et al. | |
| 2007/0134761 | A1 | 6/2007 | Chatellard et al. | |
| 2007/0196895 | A1 | 8/2007 | Aloni et al. | |
| 2007/0293658 | A1 | 12/2007 | Kornmann et al. | |
| 2008/0076708 | A1 | 3/2008 | Altarocca et al. | |
| 2008/0200658 | A1 | 8/2008 | Strat et al. | |

FOREIGN PATENT DOCUMENTS

| WO | WO 02099089 | * 12/2002 |
|---|---|---|
| WO | WO 2004/101617 A1 | 11/2004 |
| WO | WO 2005/040384 A1 | 5/2005 |
| WO | WO 2005/049649 A1 | 6/2005 |
| WO | WO 2005/083058 A1 | 9/2005 |
| WO | WO 2006/003134 A1 | 1/2006 |
| WO | WO 2006/128908 A1 | 12/2006 |
| WO | WO 2006/131550 A1 | 12/2006 |

OTHER PUBLICATIONS

Abbate, J. et al. "Bifunctional Protein Conferring Enhanced Green Fluorescence and Puromycin Resistance" *Biotechniques*, Aug. 2001, pp. 336-340, vol. 31, No. 2.
Assaraf, Y. G. et al. "Characterization of the Coexisting Multiple Mechanisms of Methotrexate Resistance in Mouse 3T6 R50 Fibroblasts" *Journal of Biological Chemistry*, Mar. 25, 1992, pp. 5776-5784, vol. 267, No. 9.
Blackwood, E. M. et al. "Going the Distance: A Current View of Enhancer Action" *Science*, Jul. 3, 1998, pp. 61-63, vol. 281, No. 5373.
DeWet, J. R. et al. "Cloning of Firefly Luciferase cDNA and the Expression of Active Luciferase in *Escherichia coli*" *Proc. Natl. Acad. Sci. USA*, 1985, pp. 7870-7873, vol. 82.
Dorsch-Hasler, K. et al. "A long and complex enhancer activates transcription of the gene coding for the highly abundant immediate early mRNA in murine cytomegalovirus" *Proc. Natl. Acad. Sci. USA*, Dec. 1985, pp. 8325-8329, vol. 82.
Li, Q. et al. "Locus control regions coming of age at a decade plus" *TRENDS In Genetics*, Oct. 1999, pp. 403-408, vol. 15, No. 10.
Mazumder, B. et al. "Translational control by the 3'-UTR: the ends specify the means" *TRENDS in Biochemical Sciences*, Feb. 2003, pp. 91-98, vol. 28, No. 2.
Messerle, M. et al. "Structure and Expression of Murine Cytomegalovirus Immediate-Early Gene 2" *Journal of Virology*, Mar. 1991, pp. 1638-1643, vol. 65, No. 3.
Kim, S.-Y. et al. "The human elongation factor 1 alpha (EF-1α) first intron highly enhances expression of foreign genes from the murine cytomegalovirus promoter" *Journal of Biotechnology*, 2002, pp. 183-187, vol. 93.
Mountford, P. S. et al. "Internal ribosome entry sites and dicistronic RNAs in mammalian transgenesis" *TRENDS in Genetics*, May 1995, pp. 179-184, vol. 11, No. 5.
Sandford, G. R. et al. "Rat Cytomegalovirus Has a Unique Immediate Early Gene Enhancer" *Virology*, 1996, pp. 310-317, vol. 222.
Schumperli, D. et al. "Efficient Expression of *Escherichia coli* Galactokinase Gene in Mammalian Cells" *Proc. Natl. Acad. Sci. USA*, Jan. 1982, pp. 257-261, vol. 79, No. 2.
Seliger, H. H. et al. "Spectral Emission and Quantum Yield of Firefly Bioluminescence" *Archives of Biochemistry and Biophysics*, 1960, pp. 136-141, vol. 88.

(Continued)

*Primary Examiner* — Maria Marvich
(74) *Attorney, Agent, or Firm* — Saliwanchik, Lloyd & Eisenschenk

(57) ABSTRACT

The invention relates to an expression vector comprising the promoter of the mCMV-IE2 gene, or a functional expression promoting fragment thereof, and/or an enhancer of the mCMV-IE2 gene, or a functional expression enhancing fragment thereof, wherein the expression vector does not contain any complete gene of the mCMV.

28 Claims, 17 Drawing Sheets

(56) References Cited

OTHER PUBLICATIONS

Shotwell, M. A. et al. "Regulation of Amino Acid Transport System L in Chinese Hamster Ovary Cells" *Journal of Biological Chemistry*, Mar. 25, 1982, pp. 2974-2980, vol. 257, No. 6.

Wood, K. V. et al. "Synthesis of Active Firefly Luciferase by In Vitro Translation of RNA Obtained from Adult Lanterns" *Biochemical and Biophysical Research Communications*, Oct. 30, 1984, pp. 592-596, vol. 124, No. 2.

Zhu, W.-Y. et al. "The Rate of Folate Receptor Alpha (FRα) Synthesis in Folate Depleted CHL Cells is Regulated by a Translational Mechanism Sensitive to Media Folate Levels, While Stable Overexpression of its mRNA is Mediated by Gene Amplification and an Increase in Transcript Half-Life" *Journal of Cellular Biochemistry*, Mar. 26, 2001, pp. 205-219, vol. 81, No. 2.

Baron, U. et al. "Co-regulation of Two Gene Activities by Tetracycline via a Bidrectional Promoter", *Nucleic Acids Research*, Sep. 11, 1995, pp. 3605-3606, vol. 23, No. 17.

Manning, W. C. et al. "Insertional Mutagenesis of the Murine Cytomegalovirus Genome: One Prominent α Gene (ie2) is Dispensable for Growth", *Virology*, 1988, pp. 477-484, vol. 167.

Urabe, M. et al. "A Novel Dicistronic AAV Vector Using a Short IRES Segment Derived from Hepatitis C Virus Genome", *Gene*, 1997, pp. 157-162, vol. 200.

Rawlinson, W.D. et al. "Analysis of the Complete DNA Sequence of Murine Cytomegalovirus" *Journal of Virology*, Dec. 1996, pp. 8833-8849, vol. 70, No. 10.

Cardin, R. D. et al. "Murine Cytomegalovirus IE2, an Activator of Gene Expression, Is Dispensable for Growth and Latency in Mice" *Virology*, 1995, pp. 236-241, vol. 209.

\* cited by examiner

```
+1        .IE2 TATA .HpaI
CACTGGGCTCGAATGGCATGGGGACAGCTTTTATATGTTAACTCCGCCCGTTTTTATGA
CTAGAACCAATAGTTTTTAATGCCAAATGCACTGAAATCCCCTAATTTGCAAAGCCAAAC
GCCCCCTATGTGAGTAATACGGGGACTTTTTACCCAATTTCCCAAGCGGAAAAGCCCCTA
ATACACTCATATGCATATGAATGACACGGTCATGCACTCTAATGCGGCCCATAGGGA
CTTTCCACATAGGGGCGTTCAACCATTCCCAGCACATAGGGGTGTGACTCAATGGCCTTT
ACCCAAGTACATTGGGTCAATGGGACTTCCACCGGGTTTGCCCAAGTACATTGGGCAAGC
ACACTGAGTGAAATGGGACTTTCCACTGGGCTGCCAAGTACACTGACTCAATAGGGACGAG
GTGAGCCAATGGGAAAAACCATTGCAGCATATAAGGTCAATGAGGGTGAATCAACAGGAAAGTCCCAT
TGGGTTTTACCATTGTTGGCCCAGTACATAAGGTCAATAAGGGGTGAATGAGGTAAGTCCCAT
CCATTGTAATCTGCCCAGTACACTGCGTCAATAGGACTTTCCAGTGGTTTGCCCAGTACATAGG
TGGAGCCAAGTACACTGCGTCAATAGGGACTTTCCAGTGGTTTGCCCAGTACATAGG
                                                      -682
TCAATAGGGGATGAGTGAGTCAATGGGAGAAAAACCCATTGGGAGCCAAGTACACTGACTCAATAGG
GACTTTCCATTGGGTTTTGCCCAGTACATTGAGTCAATAGGGGTGAGTGAATCAACAGGAAAG
TTCCATTGGAGCCAAGTACATTGAGTGAGGGACTTTCCAATGGGTTTTCCCAGTAC
ATAAGGTCAATGGGGAGGTAAGCCAAGTACCAATGGGTTTTCCCATTACTGGCACGTATACTGAGTC
ATTAGGGACTTTCCAATGGGTTTTGCCCAGTACATAAGGTCAATAGGGGTGAATCAACAG
GAAAGTCCCATTGGAGCCAAGTACACTGACTGAGTCAATAGGGACTTTCCATTGGGTTTTGCCC
AGTACAAAAGGTCAATAGGGGGTGAGTCATTGGGTTTTTTCCAGCCAAT-AATTAAACGCCATGTACT
AGGTCAATAGGGGTGAGTGGGTGAGTCATTGGGTTTTTCCAGCCAAT-TAATTAAAACGCCATGTACT
TTCCCACCATTGACGTCAATGGGCTCATTGGGAAAGTACCTTGAGAAC-AATGCAACGTGACCTTTAACGTAC
                                                          XhoI
TTTCCCATAGCTGATTAATGGGAGAAAGTACCGTTCTCGAGCCAATACACGTCAATGGGAAG
                                                  IE1 TATA
TGAAAGGGCAGCCAAAAACGTAACACCGCCCCGTTTTCCCCTGAAATTCCATATTGGCA
CGCATTCTATTGGCTCAGCTCCGTTCTACGTGGCTATAAGAGGCCGACCAGCGTCGGTA
+1 IE1
CCGTCGCAGTCTTG
```

FIG. 1

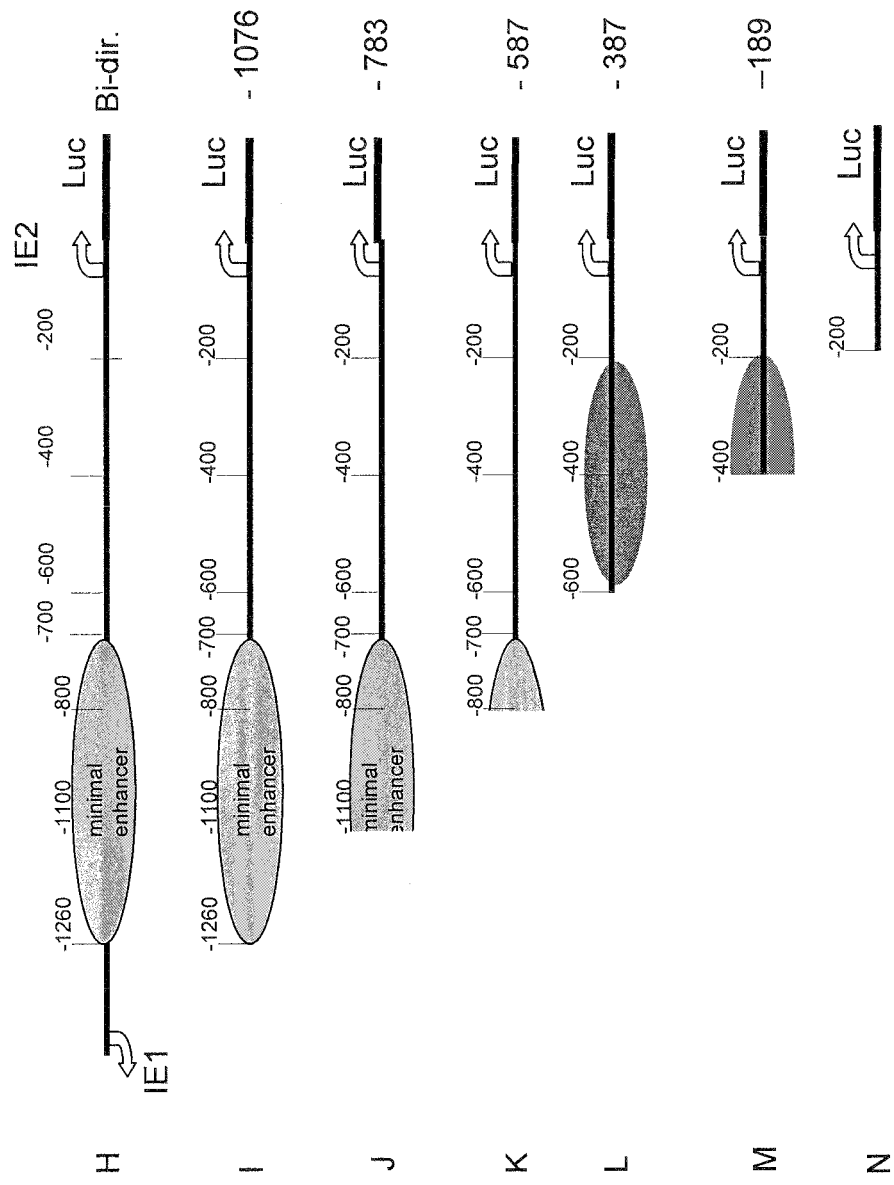
Fig. 10.a

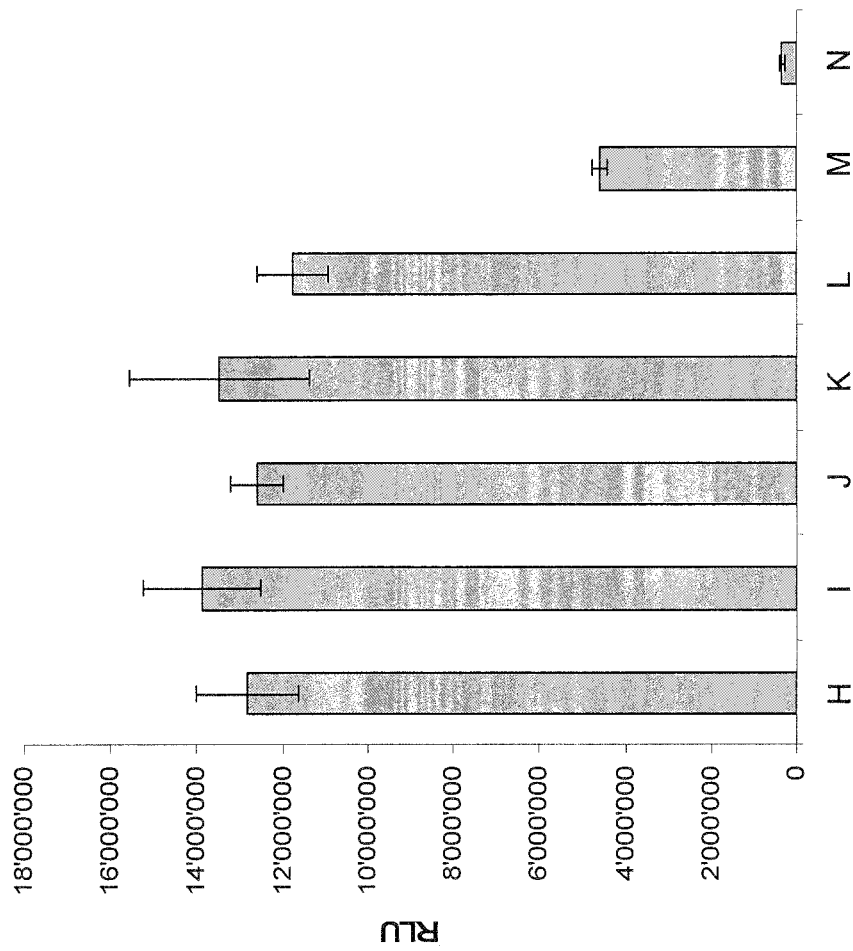
Fig. 10.b

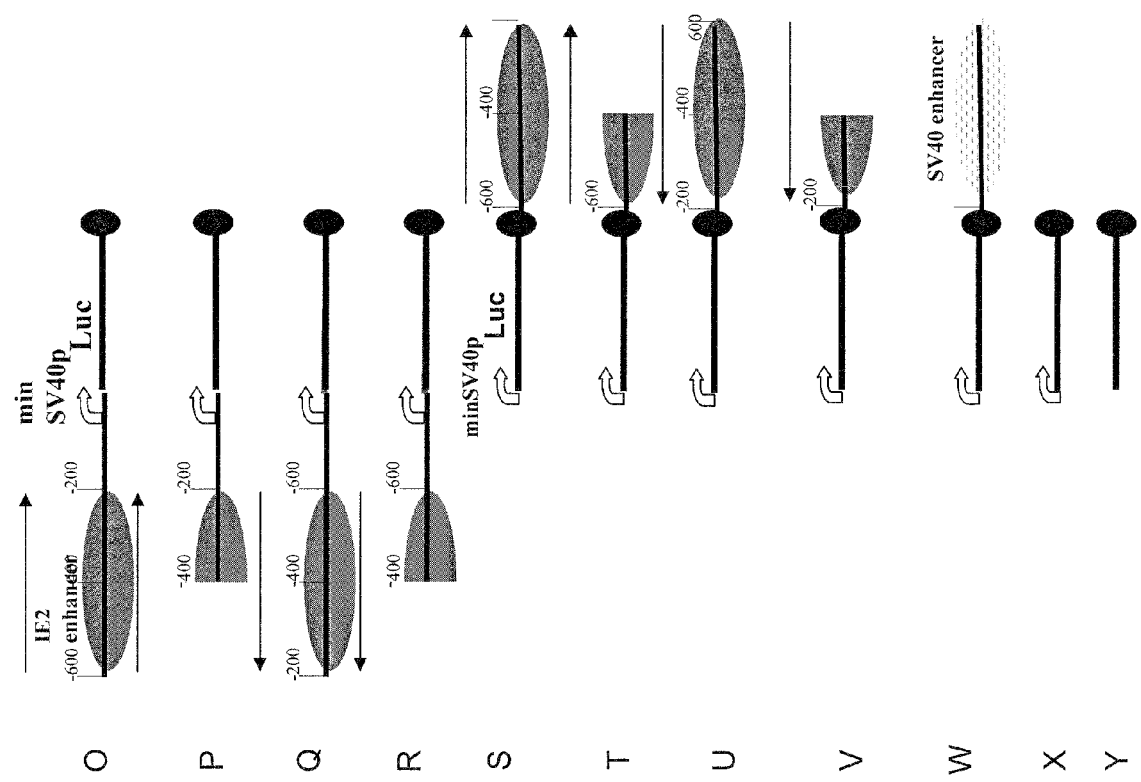
Fig. 11.a

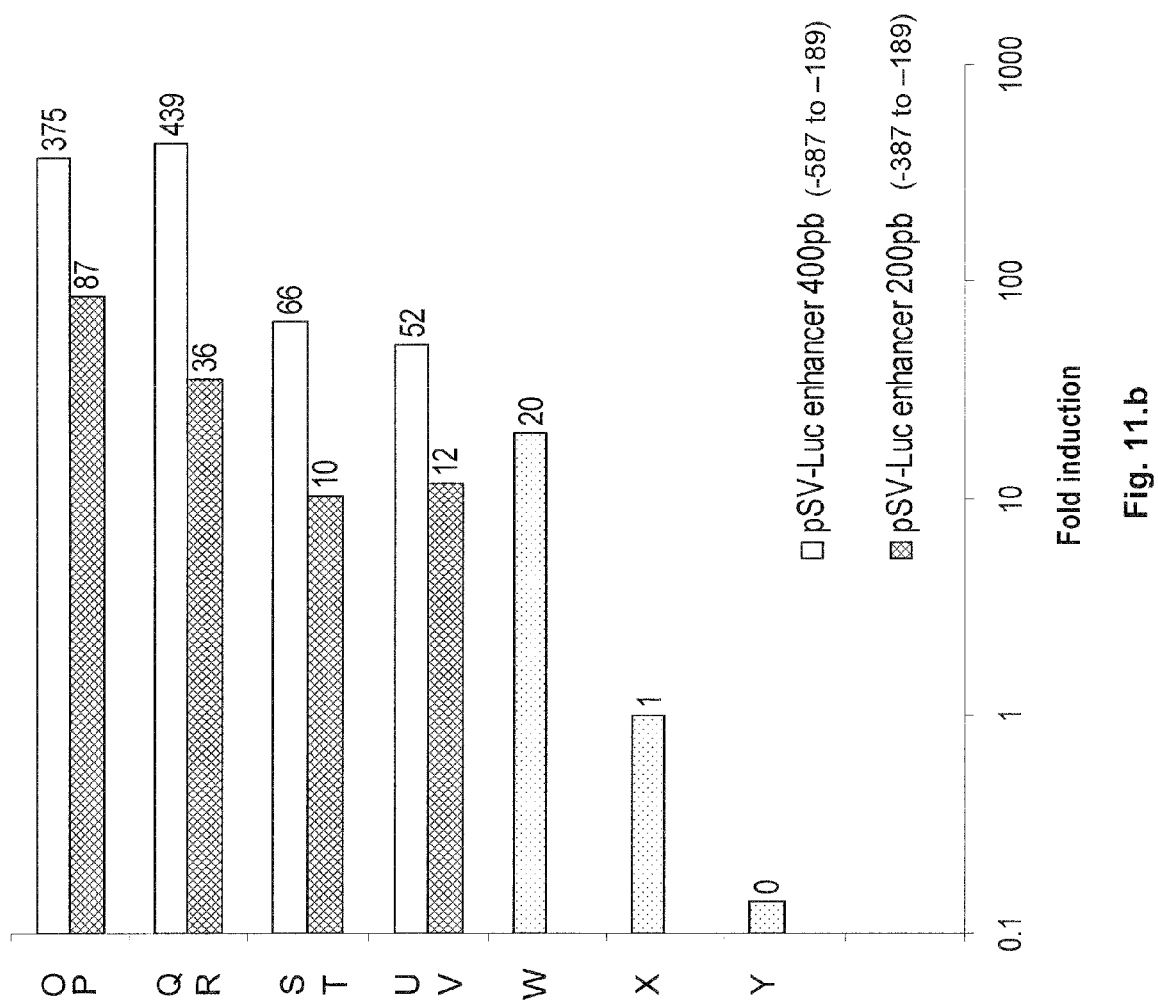
Fig. 11.b

EXPRESSION VECTORS COMPRISING THE MCMV IE2 PROMOTER

CROSS-REFERENCE TO RELATED APPLICATIONS

This application is a continuation of U.S. Ser. No. 10/548,364, filed Jan. 26, 2006, now U.S. Pat. No. 7,824,907, which is the U.S. national stage application of International Patent Application No. PCT/EP2004/050280, filed Mar. 10, 2004, the disclosures of which are hereby incorporated by reference in their entirety, including all figures, tables and amino acid or nucleic acid sequences.

FIELD OF THE INVENTION

The invention relates to expression vectors comprising the promoter of the mCMV-IE2 gene, or a functional expression promoting fragment thereof, and/or an enhancer of the mCMV-IE2 gene, or a functional expression enhancing fragment thereof, wherein the expression vector does not contain any complete gene of the mCMV, to host cells containing such vectors, to methods of producing desired polypeptides by using these expression vectors, and to uses of said expression vectors.

Expression vectors comprising the mCMV IE2 promoter and the mCMV IE1 promoter, optionally together with the new mCMV IE2 enhancer, are preferred in accordance with the invention, particularly if both promoters are arranged in a bi-directional architecture.

BACKGROUND OF THE INVENTION

Since decades, expression vectors have been used as vehicles for the expression of genes or cDNAs encoding polypeptides or proteins of interest in host cells. Strong viral or cellular promoters and enhancers are being used to express the gene of interest at high levels by using transient or stable transfection of recombinant DNA into the host cells. The immediate early (IE) region of the human cytomegalovirus (hCMV) has been shown to be particularly suitable in this regard, and expression vectors comprising gene elements derived from this region are known e.g. from EP0323997B1.

Until today, the gene regulatory sequences from the murine cytomegalovirus (mCMV) have been used rarely, although mCMV derived regulatory elements were identified to be very powerful and even stronger than the human counterpart (Kim et al. 2002).

U.S. Pat. No. 4,963,481 (de Villiers) discloses expression vectors having a DNA encoding a heterologous protein under the transcriptional control of DNA fragments derived from the mCMV IE gene region including an approximately 2270 base pair (bp) restriction endonuclease PstI fragment isolated from the viral genome. A 1387 bp truncated version of this fragment resulted in significant improvement in the efficacy of the DNA fragment as a promoter for expression of the heterologous protein.

U.S. Pat. No. 4,968,615 (Kozinowski) describes recombinant DNA molecules containing transcription enhancers from murine cytomegalovirus (MCMV) which can be used to enhance the transcription of structural genes in eukaryotic cells. The mCMV enhancer was said to be located within the 2.27 kb PstI fragment identified by de Villiers (U.S. Pat. No. 4,963,481).

Manning and Mocarski (1988) analysed the functional importance of the mCMV IE2 region for replication of the murine cytomegalovirus. To this end, a recombinant virus was constructed having the lacZ reporter gene under the transcriptional control of the mCMV IE enhancer/promoter, thus disrupting the IE2 gene. Indeed no IE2 gene expression could be observed, and the virus replicated normally. The authors thus concluded that the IE2 gene, that is not conserved among the cytomegaloviruses such as the mCMV and the hCMV, was not essential for virus replication. No indication of any particular utility of the IE2 enhancer/promoter region was disclosed or suggested by Manning and Mocarski.

More recent literature shows a further difference between the mouse and human CMV IE region. The mouse locus expresses a second major mRNA in the opposite direction of the first IE gene. This second immediate early gene was termed IE2, and its promoter sequence referred to as IE2 promoter (Messerle et al. 1991).

The IE2 region from the mCMV has not been used in vectors for expression of heterologous proteins so far.

SUMMARY OF THE INVENTION

The present invention is based on the finding that a vector having a DNA element comprising the IE2 promoter region of the mCMV can efficiently drive the expression of a gene of interest in transfected host cells.

The invention is further based on the identification of a new enhancer in the mCMV IE2 region, which is herein called the mCMV IE2 enhancer. This enhancer fulfills the criteria commonly applied for enhancer definition, i.e. enhancing expression independently from (1) location, (2) orientation, and (3) enhancing the expression from a heterologous promoter.

Therefore, a first aspect of the invention relates to an expression vector comprising the promoter of the mCMV-IE2 gene, or a functional expression promoting fragment thereof, and/or an enhancer of the mCMV-IE2 gene, or a functional expression enhancing fragment thereof, wherein the expression vector does not contain any complete gene of the mCMV.

In a second aspect, the invention relates to a host cell comprising a vector according to the invention.

A third aspect of the invention relates to a process for the production of a polypeptide of interest comprising the step of transfecting a host cell with a vector in accordance with the invention.

In a fourth aspect, the invention relates to a process for the production of a polypeptide of interest comprising the step of culturing the host cell of the invention.

A fifth aspect of the invention relates to the use of a vector in accordance with the invention for expression of one or more genes or cDNAs of interest.

In a sixth aspect, the invention relates to the use of a vector of the invention for selection of clones that express high amounts of a gene of interest.

A seventh aspect relates to the use of a vector in accordance with the present invention in DNA-based therapy.

BRIEF DESCRIPTION OF THE DRAWINGS

FIG. 1 shows the sequence of a bi-directional DNA element derived from the mCMV IE region for use in expression constructs (SEQ ID NO: 1). The +1 sites and TATA boxes of the IE2 and IE1 promoters are indicated, respectively. The core promoters for both genes are shown in a box. HpaI and XhoI restriction sites are shown in bold. The −682 position is indicated with respect to +1 of IE1.

A: The negative promoter-less control (pGL3 Basic).
B: An SV40 promoter/enhancer driven luciferase reporter vector (pGL3 Control).
C: Luciferase expression IE1 promoter driven (pmCMV Luciferase, IE1 driven).
D: Luciferase expression IE2 promoter driven (prevmCMV Luciferase, IE2 driven).
E: Luciferase expression IE2 promoter driven, IE1 promoter deleted (prevmCMV Luciferase (ΔXhoI), IE2 driven, IE1 minus).
F: Luciferase expression IE1 promoter driven, and IE2 promoter deleted (pBS.MCMV3 Luciferase, IE1 driven (1.4 kb), IE2 minus).
G: A short version of the IE1 promoter drives Luciferase expression (p-680 Luciferase, IE1 driven (short version, 0.68 kb)).

Figure 2:
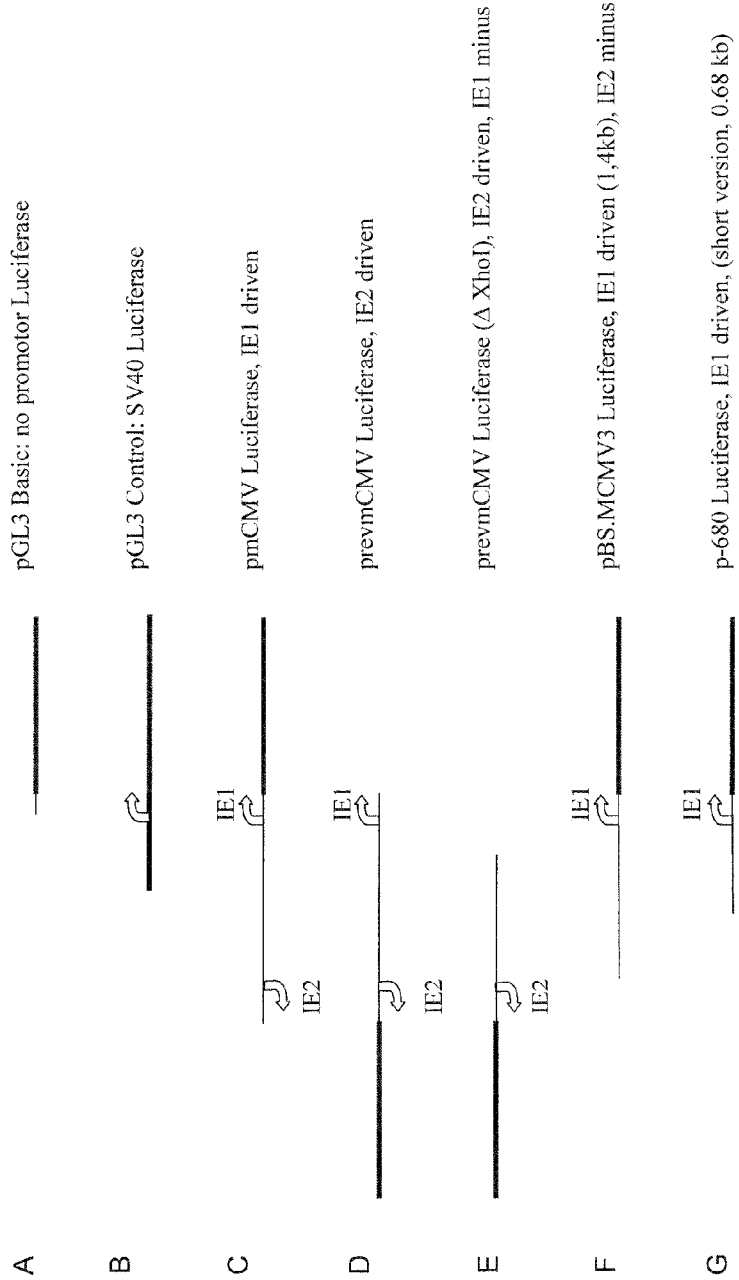
FIG. 2 shows the reporter constructs A to G. The luciferase reporter gene is shown as a bold line and promoters are indicated as open arrows.
Figure 3:
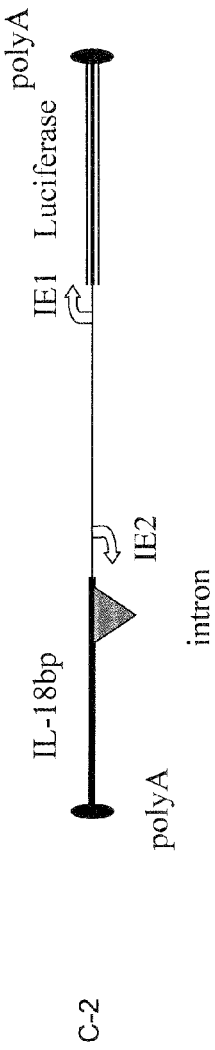

FIG. 3 shows a bi-directional construct similar to construct C of FIG. 2 (construct C-2) with the coding sequence for IL-18BP (bold line) linked to the IE2 promoter. Thus, in this construct, the mCMV IE1 promoter drives luciferase expression, and simultaneously the mCMV IE2 promoter drives IL-18BP expression. Triangle: intron. Closed ovals: polyA.

Figure 4:
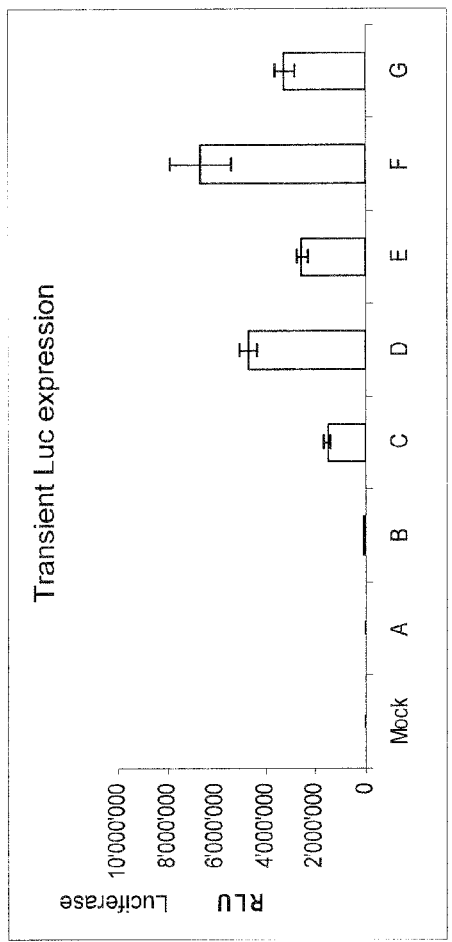

FIG. 4 shows the Luciferase reporter gene expression from the different reporter constructs that are depicted in FIG. 2, constructs A to G. CHO-S cells grown in a serum-free medium (SFM) were transiently transfected with constructs A to G, or mock transfected. Luciferase activity is expressed as RLU=relative light units.

Figure 5:
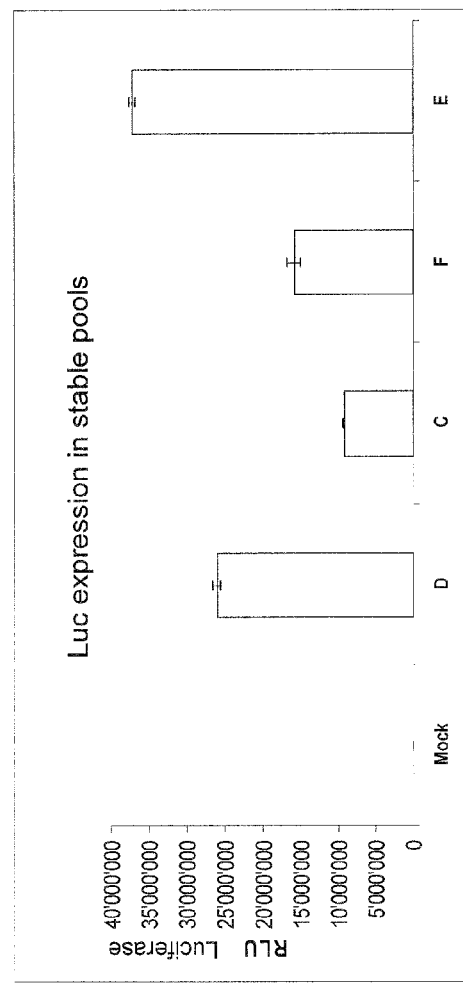

FIG. 5 shows Luciferase expression measured as RLU in stable pools of transfected CHO-S cells. The cells were grown in SFM after transfection with constructs D, C, F and E, as depicted in FIG. 2. Luciferase expression was assessed after 21 days of selection.

Figure 6:
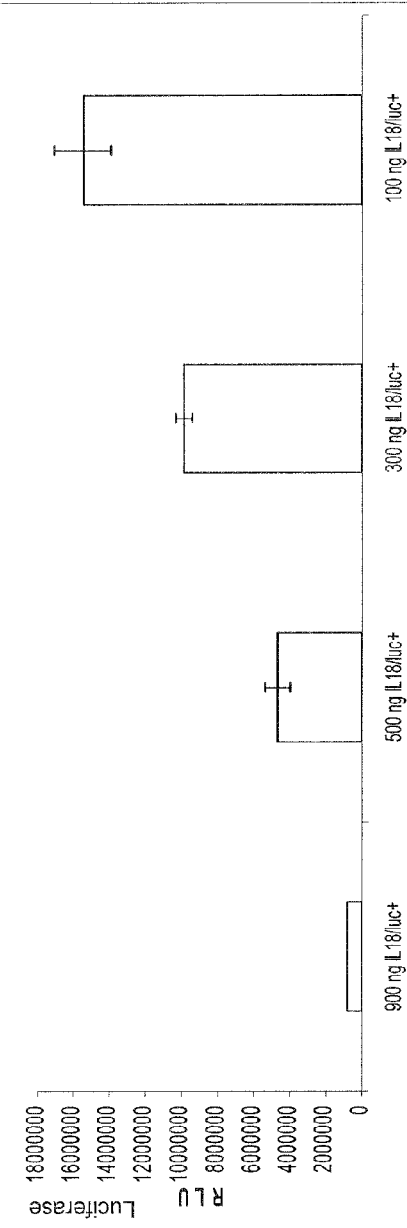

FIG. 6 shows Luciferase expression measured as RLU after transient transfection with 900, 500, 300 and 100 ng of the bi-directional construct C-2 shown in FIG. 3.

Figure 7:
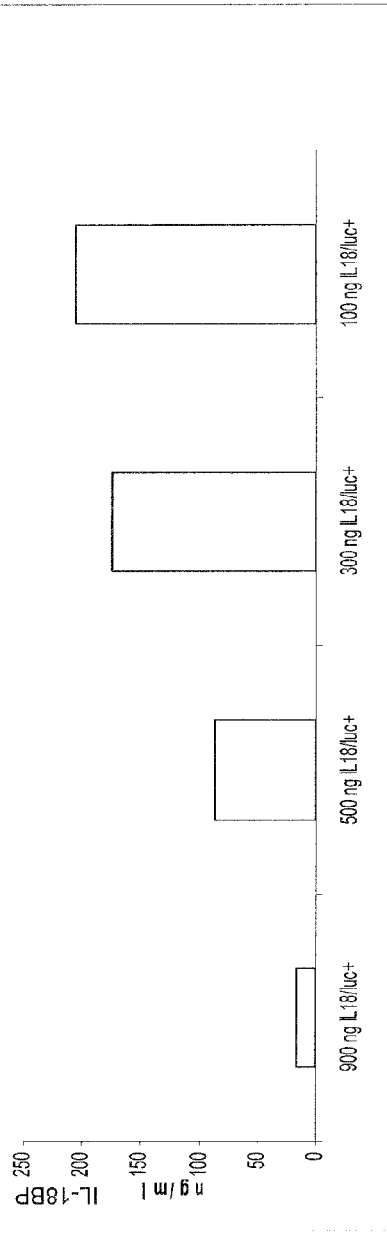

FIG. 7 shows the amount of IL-18BP in ng/ml in the cell culture supernatants from the transient transfection experiment according to FIG. 6 (construct C-2).

Figure 8:
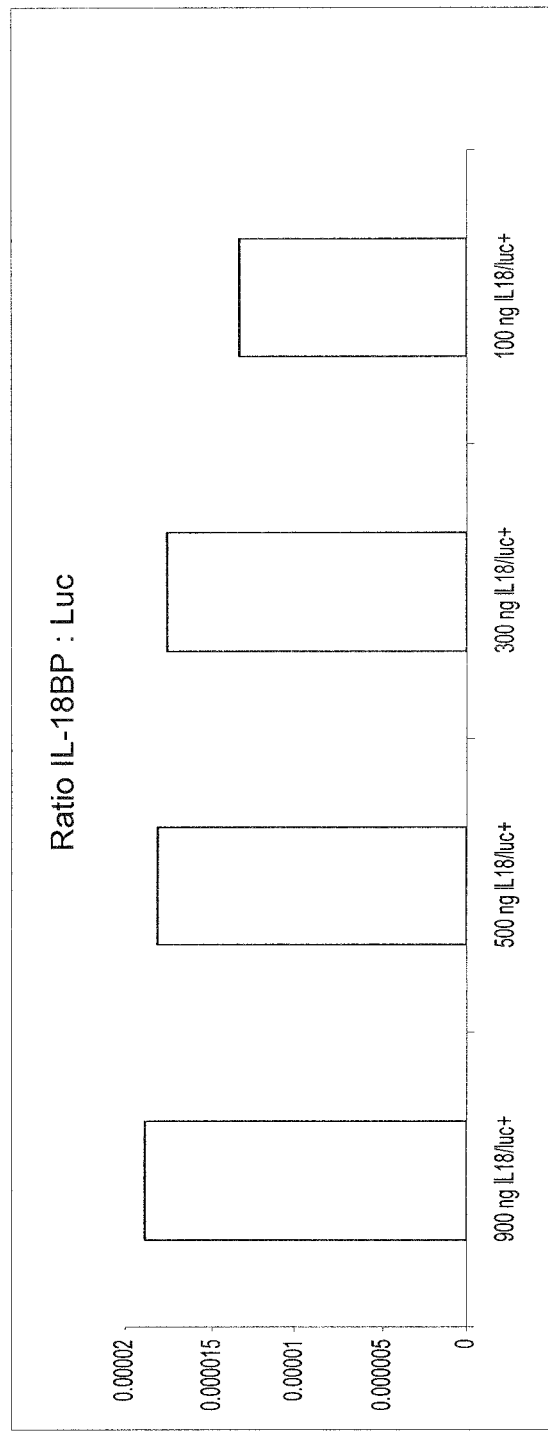

FIG. 8 shows the ratio of the amounts of IL-18BP versus Luciferase measured in the experiment according to FIGS. 6 and 7.

Figure 9:
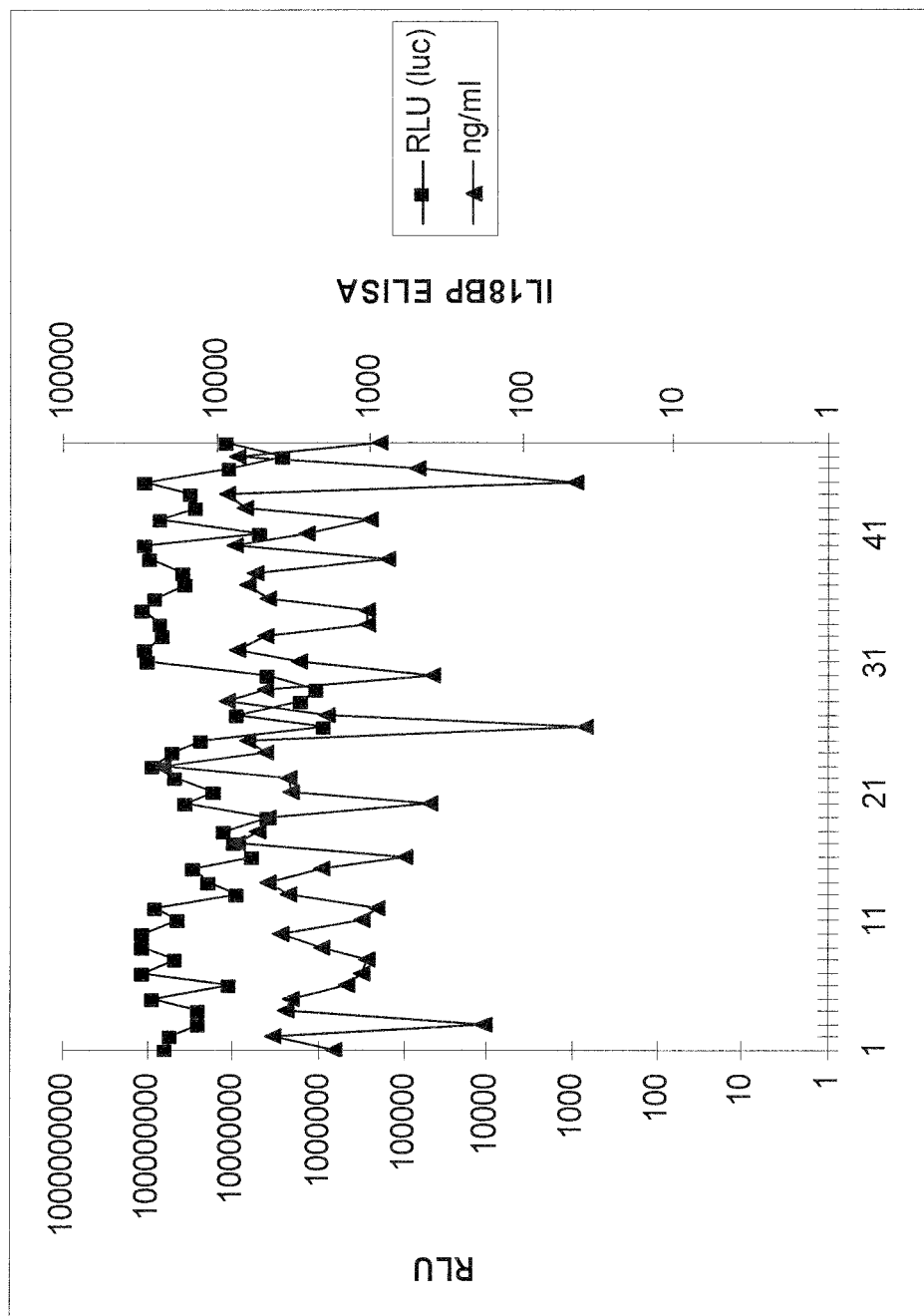

FIG. 9 shows the amounts of Luciferase in RLU (left y axis) and IL-18 BP in ng/ml (right y axis) expressed by 48 individual clones that were picked 8 days after transfection with the bi-directional construct C-2 (as shown in FIG. 3). The detection limit for Luciferase was about 500 RLU, and 2.5 ng/ml for IL-18BP. Each increment on the X axis represents one single clone.

FIG. 10 (a) shows the reporter constructs H to N. The luciferase reporter gene (Luc) is shown as a bold line and the respective IE1 and IE2 promoters are indicated as open arrows. Enhancers are shown as gray ovals: Light gray for the known IE1 enhancer, and dark gray for the new IE2 enhancer.
H: Bidirectional construct with IE2 promoter driven Luciferase expression;
I: Luciferase expression was IE2 promoter driven, and the IE1 promoter was deleted;
J, K, L, M, N: constructs contained shortened mCMV promoters, the positions corresponding to the number of base pairs from mCMVp, relative to the +1 of IE2 as reference:
J: from −1076
K: from −783
L: from −587
M: from −387
N: from −189

FIG. 10 (b) shows Luciferase expression in RLU from reporter constructs H to N according to FIG. 10 (a), after transient transfection of CHO-S cells that were grown in a serum-free medium.

FIG. 11 (a) shows further reporter constructs O to Y that combined the new IE2 enhancer (gray oval) with the SV40 promoter. The gray oval represents the IE2 enhancer from −587 to −189, the half gray oval represents the IE2 enhancer from −387 to −189. The arrow above the IE2 enhancer indicates the direction of the enhancer sequence. The luciferase reporter gene is shown as a bold line, the SV40 promoter is indicated as an open arrow. Black oval: polyA.
O: long IE2 enhancer sequence (−587/−189) cloned 5' of SV40 promoter;
P: short IE2 enhancer sequence (−387/−189) cloned 5' of SV40 promoter;
Q: long IE2 enhancer sequence (−587/−189) cloned 5' of SV40 promoter in the reverse orientation;
R: short IE2 enhancer sequence (−387/−189) cloned 5' of SV40 promoter in the reverse orientation;
S: long IE2 enhancer sequence (−587/−189) cloned 3' of the Luciferase gene;
T: short IE2 enhancer sequence (−387/−189) cloned 3' of the Luciferase gene;
U: long IE2 enhancer sequence (−587/−189) cloned 3' of the Luciferase gene in the reverse orientation;
V: short IE2 enhancer sequence (−387/−189) cloned 3' of the Luciferase gene in the reverse orientation;
W: Control, SV40 promoter and SV40 enhancer in 3' of the Luciferase coding sequence
X: Control, Luciferase expression driven by SV40 promoter without any enhancer
Y: negative control, no promoter at all.

FIG. 11 (b) shows Luciferase expression from reporter constructs O to Y as shown in FIG. 11 (a). CHO-S cells grown in a serum-free medium (SFM) were transiently transfected with constructs O to Y. Luciferase activity is expressed as fold induction as compared to the control X (value 1), i.e. expression driven by the SV40 promoter without any enhancer. Open bars: long IE2 enhancer (−587 to −189), hatched bars: short IE2 enhancer (−387 to −189). X axis is a logarithmic scale.

Figure 12:
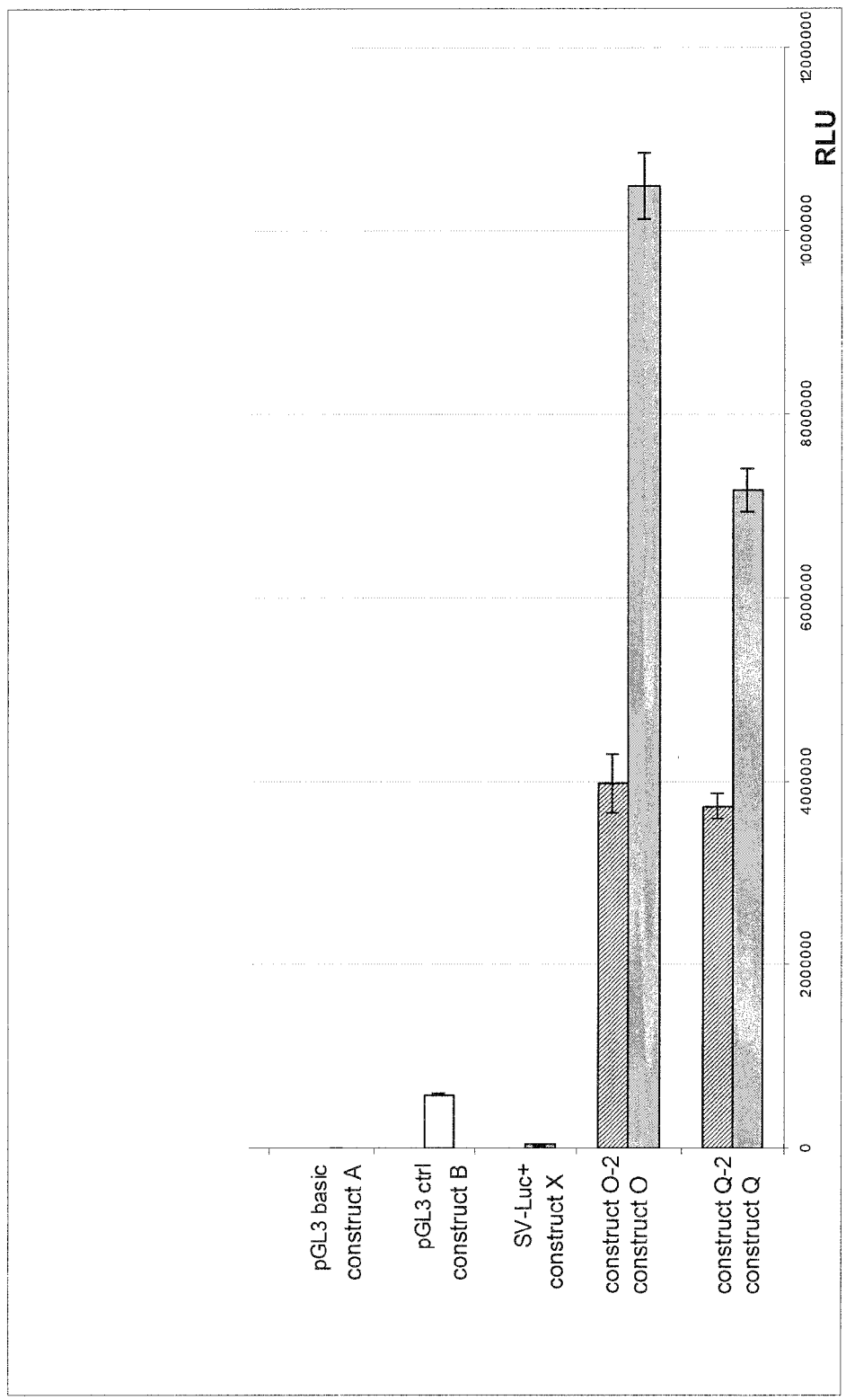

FIG. 12 shows an experiment comparing the new IE2 enhancer with the known hCMV enhancer. Cells were transfected with control construct A (pGL3 basic, see FIG. 2, promoterless), control construct B (pGL3 ctrl, see FIG. 2, SV40 promoter with the SV40 enhancer sequence in 3' of the luciferase coding region), control construct X (SV-Luc+, see FIG. 11.a, SV40 promoter without enhancer), as well as constructs O and Q (see FIG. 11 a) or constructs O-2 and Q-2, in which the IE2 enhancer sequence (long version, −587 to −189) was replaced by the known hCMV enhancer sequence (SEQ ID NO: 2). Luciferase were measured in RLU (x axis). Hatched bars: with known hCMV enhancer. Gray bars: with new IE2 enhancer.

Figure 13:
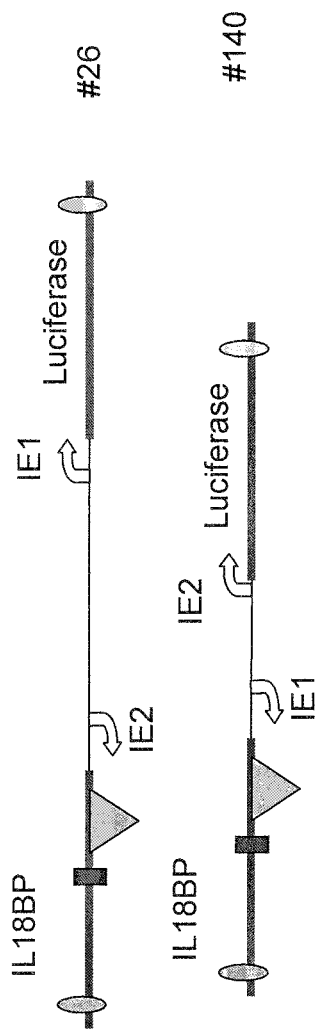

FIG. 13 shows the bi-directional vector used for simultaneous expression of IL-18BP and Luciferase. IE1 and IE2 promoters are indicated as open arrows. The triangle represents intron A from the hCMV IE region, and the gray oval the polyadenylation signal. The closed square represents the signal peptide.
Construct #26: Luciferase expressed from IE1 promoter and IL-18BP from IE2 promoter.
The sequence between both promoters is as in construct H of FIG. 10.a.
Construct #140: Luciferase expressed by IE2 promoter and IL-18BP from IE1 promoter.

The IE2 enhancer (−587 to −189) is located between the two promoters.

Figure 14:
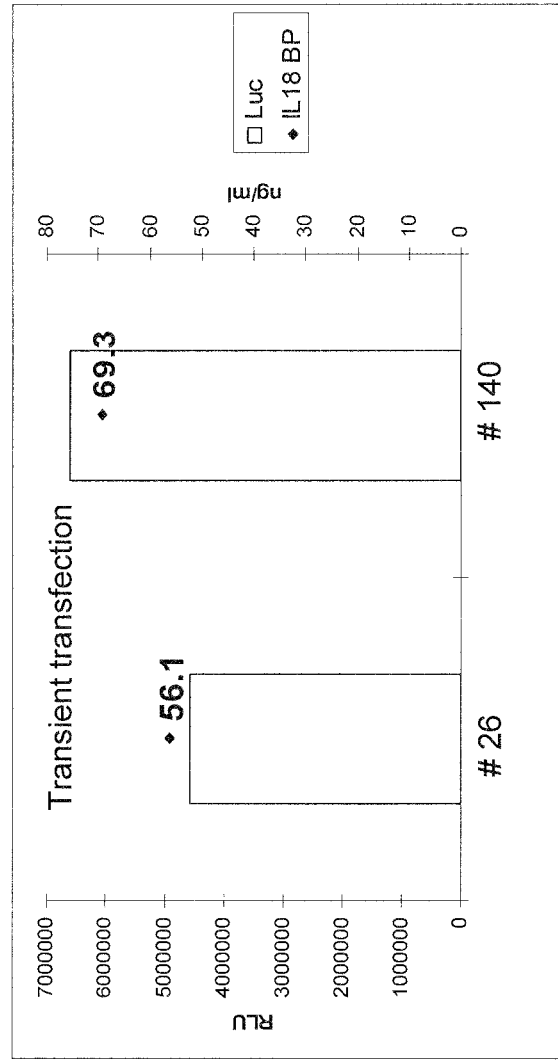

FIG. 14 shows the amounts of expressed Luciferase (RLU, left y axis) and IL-18BP (ng/ml, right Y axis) after transient transfection of CHO cells grown in serum-free medium with either construct #26 or #140 according to FIG. 13. Bars: Luciferase expression, closed lozenges: IL-18BP expression.

Figure 15:
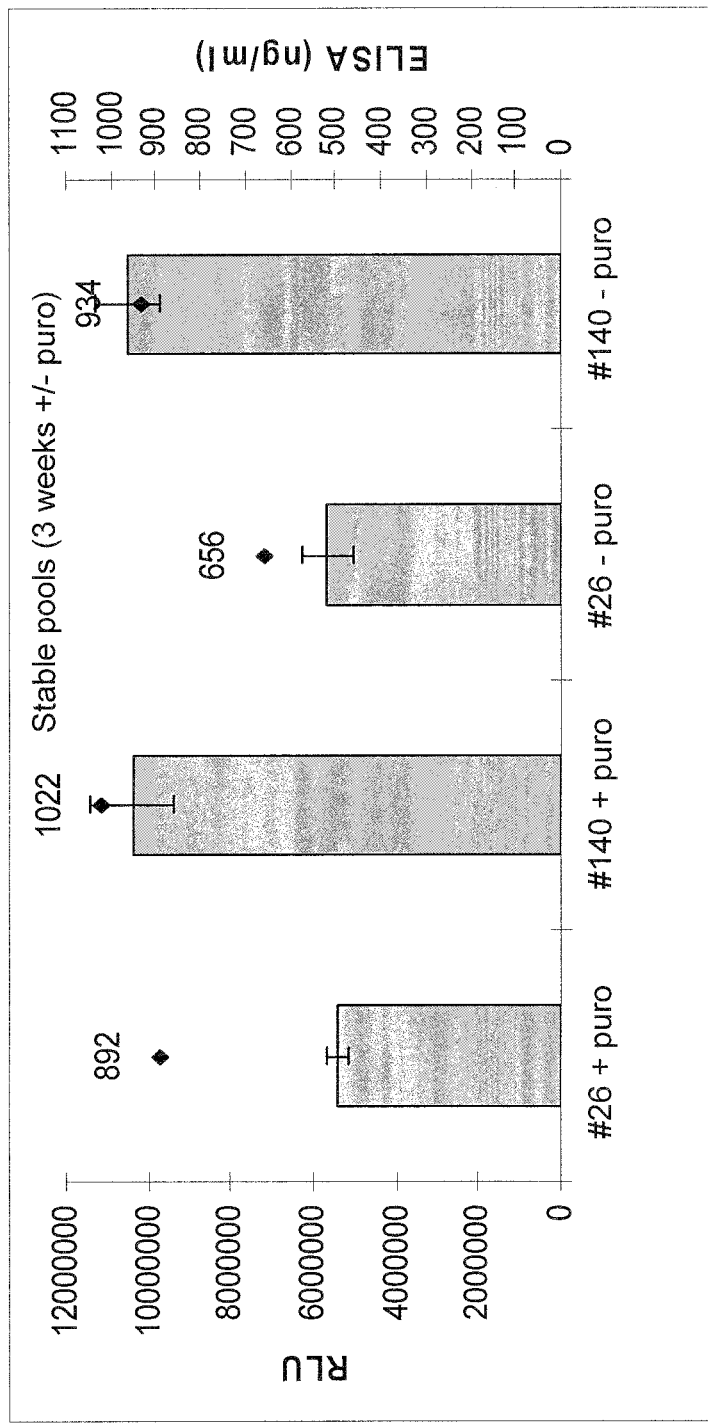

FIG. 15 shows expression of luciferase (RLU, left y axis) and IL-18BP (ng/ml, right y axis) in stable pools transfected with either construct #26 or #140 according to FIG. 13. Expression was measured 7 weeks post-transfection. The cells were kept under selection with puromycin (+puro), or for 3 weeks without puromycin selection (−puro). Bars: Luciferase expression, closed lozenges: IL-18BP expression.

Figure 16:
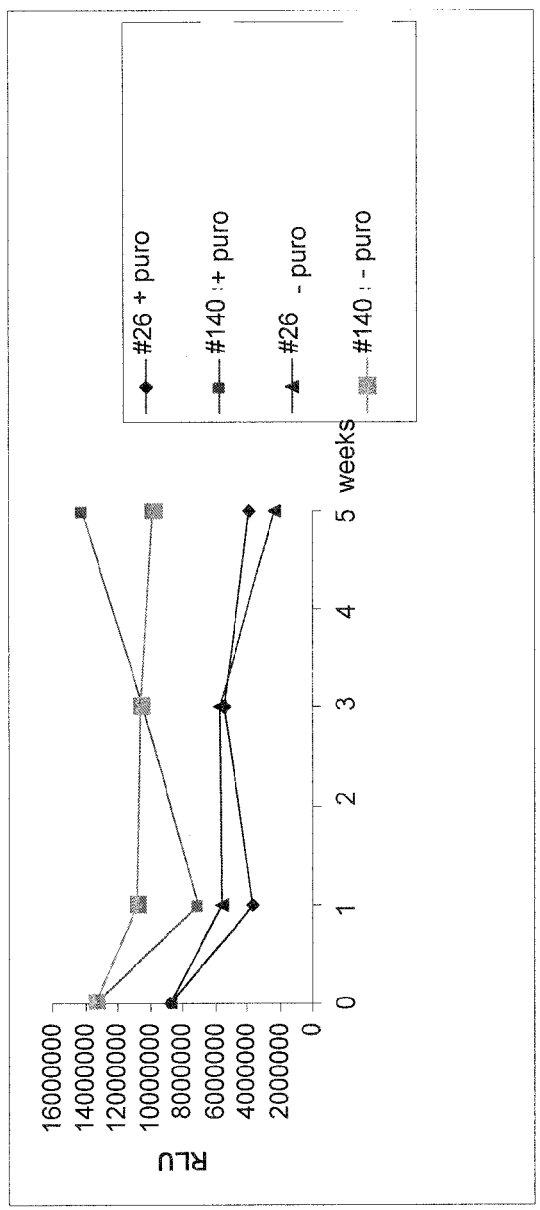

FIG. 16 shows the time course of Luciferase expression as in experiment of FIG. 15. The x axis represents time in weeks. The data shown in FIG. 15 correspond to the 3 weeks date in FIG. 16. Closed lozenge: #26+puro, small square: #140+puro, closed triangle: #26−puro, large square: #140−puro.

Figure 17:
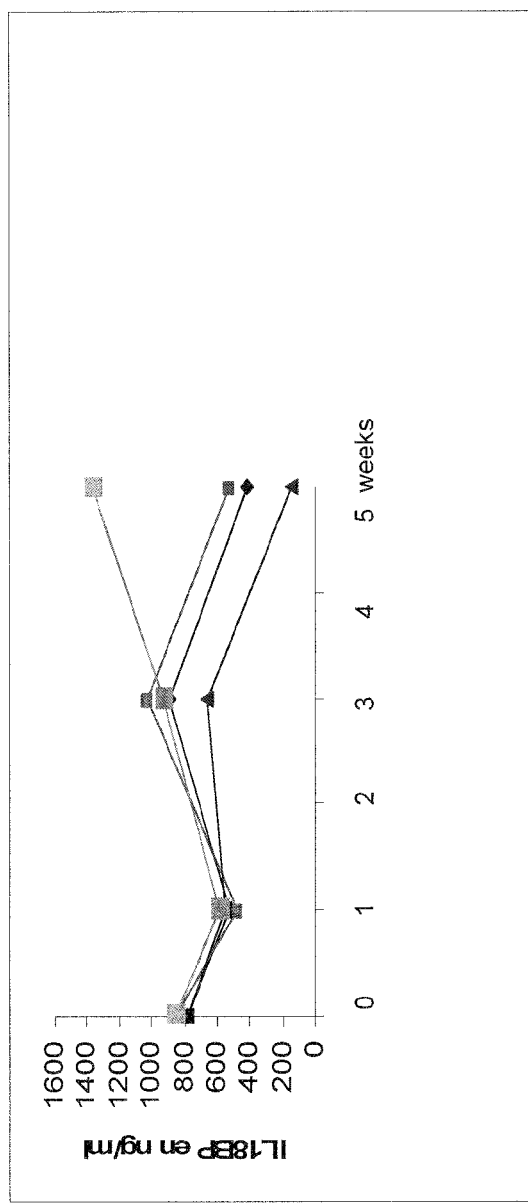

FIG. 17 shows time course of IL-18BP expression in the experiment according to FIG. 16 legend as in FIG. 16.

Figure 18:
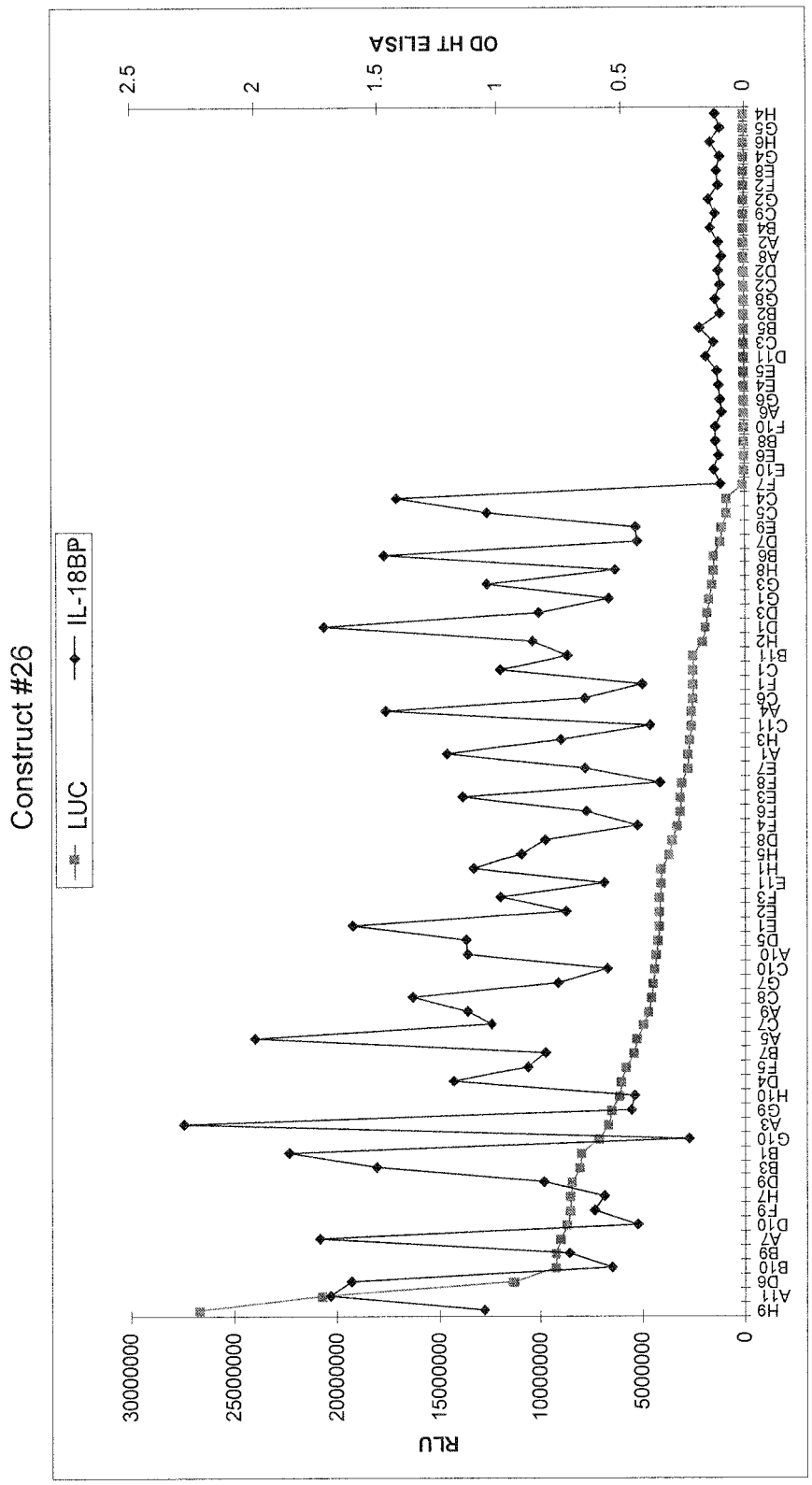

FIG. 18: Individual proto-clones were analyzed for luciferase expression (squares) in RLU (left y axis) and IL-18BP expression (lozenges) in ng/ml (right y axis). Each increment on the x axis represents and individual proto-clone. Protoclones were established from CHO cells stably transfected with construct #26 and were kept under puromycin selection.

Figure 19:
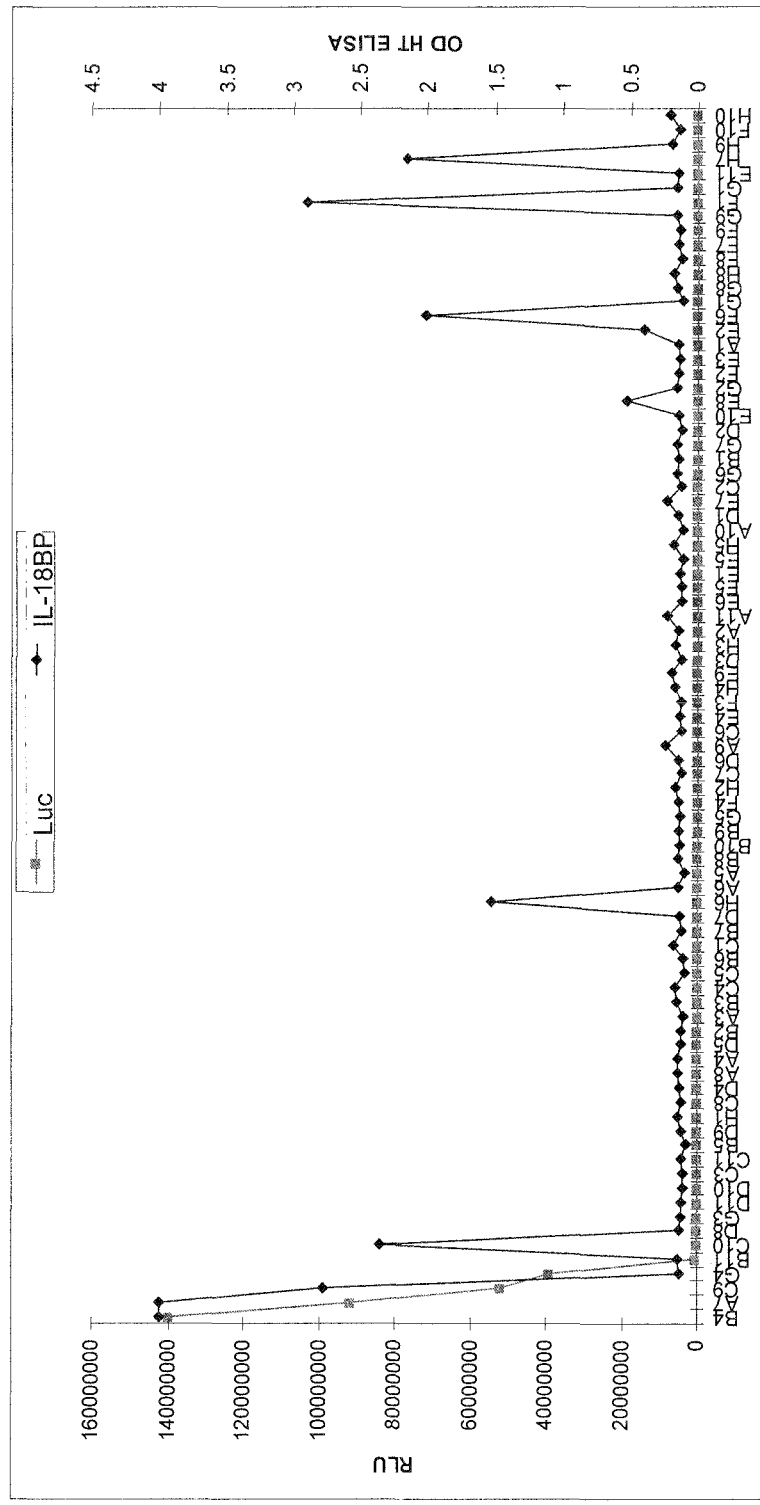

FIG. 19: As FIG. 18, but protoclones were established from cells transfected with construct #140.

Figure 20:
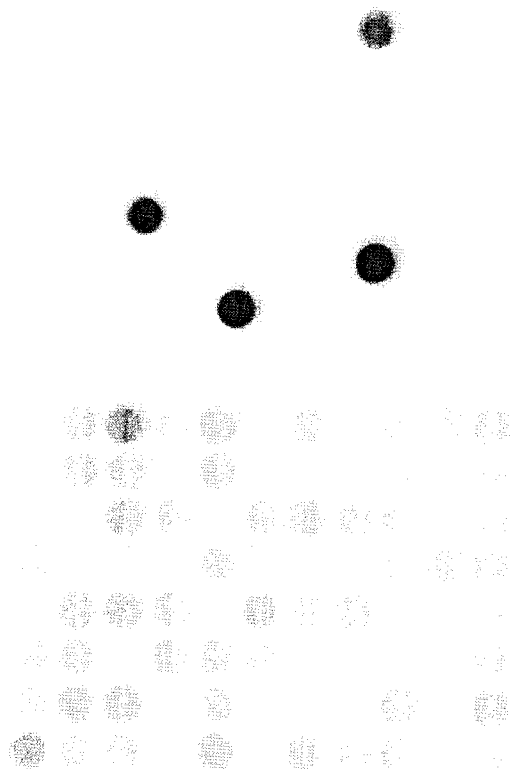

FIG. 20: The protoclones transfected either with construct #26 or #140 were analyzed for Luciferase expression in a 96 well format, inverted ChemiDoc view.

DETAILED DESCRIPTION OF THE INVENTION

In accordance with the present invention, is has been surprisingly found that the promoter of the immediate early two (IE2) gene of the murine cytomegalovirus (mCMV) is efficient in promoting the expression of a polypeptide of interest that is not the mCMV IE2 protein itself, i.e. of a heterologous polypeptide or protein. This expression vector is not supposed to be the murine cytomegalovirus itself, or contain any complete mCMV viral genes, but it is a vector conceived for recombinant protein expression.

Therefore, the invention relates to an expression vector comprising the promoter of the mCMV-IE2 gene, or a functional expression promoting fragment thereof, wherein the expression vector does not contain any complete gene of the mCMV.

In addition to this, a new enhancer has been identified in the mCMV IE2 region, which is called herein the mCMV IE2 enhancer, or the IE2 enhancer. This enhancer enhances expression irrespective of its location or orientation vis-à-vis the gene, and enhances expression from heterologous promoters, thus fulfilling the general criteria of an enhancer.

The invention therefore also relates to an expression vector comprising the enhancer of the mCMV-IE2 gene, or a functional expression enhancing fragment thereof, wherein the expression vector does not contain any complete gene of the mCMV.

The person skilled in the art will appreciate that the vector of the invention may comprise the mCMV IE2 promoter alone, or in combination with any appropriate known enhancer. The person skilled in the art will also appreciate that the vector of the invention may comprise the mCMV IE2 enhancer alone, or in combination with any suitable promoter. In addition, the vector of the invention may comprise the mCMV IE2 promoter in combination with the mCMV IE2 enhancer.

The mCMV IE2 gene itself is known e.g. from Messerle et al., 1991.

The term "promoter" as used herein refers to a region of DNA that functions to control the transcription of one or more DNA sequences, and that is structurally identified by the presence of a binding site for DNA-dependent RNA-polymerase and of other DNA sequences, which interact to regulate promoter function. A functional expression promoting fragment of a promoter is a shortened or truncated promoter sequence retaining the activity as a promoter. Promoter activity may be measured in any of the assays known in the art, e.g. in a reporter assay using Luciferase as reporter gene (Wood, 1991; Seliger and McElroy, 1960; de Wet et al. (1985), or commercially available from Promega®).

In accordance with the present invention, the IE2 promoter may e.g. comprise a sequence spanning from position +1 to the TATA box as indicated in FIG. 1. The IE2 promoter may also comprise a sequence herein called "core promoter" spanning from nucleotide 1 to 39 of the sequence depicted in FIG. 1 (box). The person skilled in the art will appreciate that the sequence of the mCMV IE2 promoter may be longer or shorter than the core promoter, as long as it drives transcription of a DNA sequence operably linked thereto. For instance, the IE2 promoter may also comprise 100-200 base pairs upstream of the core promoter. Such promoter region is also called the "proximal promoter". The person skilled in the art will further appreciate that the terms "promoter" and "enhancer" (see below) are not exactly defined and that thus the promoter may comprise enhancer regions, or enhancer regions may comprise promoter regions, depending on nomenclature and context.

The term "vector" refers to any carrier of exogenous DNA or RNA that is useful for transferring exogenous DNA to a host cell for replication and/or appropriate expression of the exogenous DNA by the host cell.

The term "operably linked" as used herein means functionally fusing a promoter with a structural gene or cDNA or any other DNA sequence to be transcribed in the proper frame to express the gene, cDNA or other DNA under control of the promoter. The term operably linked, as used herein, is thus not limited to a direct fusion of DNA sequences.

The term "complete gene of the mCMV" refers to a viral gene of the murine cytomegalovirus that has its own (endogenous, viral) 5' and 3' regulation elements.

An "enhancer region" refers to a region of DNA that functions to increase the transcription of one or more genes. More specifically, the term "enhancer", as used herein, is a DNA regulatory element that enhances, augments, improves, or ameliorates expression of a gene irrespective of its location and orientation vis-à-vis the gene to be expressed, and may be enhancing, augmenting, improving, or ameliorating expression of more than one promoter. Preferably, the enhancer enhances expression from more than one promoter simultaneously. A functional expression enhancing fragment of an enhancer is a shortened or truncated enhancer sequence retaining the enhancing activity.

The vector of the invention preferably comprises a fragment including nucleotides −387 to −189 of the mCMV IE2 upstream region, the nucleotide numbering being relative to +1 of IE2 gene. This is fragment has enhancer function, and it is herein also called IE2 enhancer short version.

In a further preferred embodiment, the vector comprises a fragment including nucleotides −587 to −189 of the mCMV IE2 upstream region, the nucleotide numbering being relative to +1 of IE2 gene. This fragment has enhancer function, and it is herein also called IE2 enhancer long version.

The vector of the invention may also comprise yet a further mCMV IE enhancer, or a functional expression enhancing fragment thereof, herein called the "CMV IE1 enhancer".

Such a mCMV IE1 enhancer is known in the art, e.g. from U.S. Pat. No. 4,968,615. It may e.g. span from position −587 to −147, or from position −682 to −147 of the sequence shown in FIG. 1, the numbering being relative to +1 position of the IE1 gene. The mCMV IE1 enhancer that may be used in accordance with the present invention may further comprise a sequence spanning from base pair −1330 to −488, relative to position +1 of the IE1 in FIG. 1. The enhancer region may comprise all or part of a promoter as well.

By using a mCMV enhancer in addition to the IE2 promoter, expression of the polypeptide of interest may further be increased.

In accordance with the present invention, the vector further comprises a promoter that is different from the mCMV-IE2 promoter, or a functional expression promoting fragment thereof.

In a preferred embodiment, the vector of the invention comprises a first and a second promoter of viral, cellular or artificial origin, or a functional expression promoting fragment thereof.

In accordance with the present invention, it has been shown that the presence of a second promoter leads to efficient expression of a polypeptide of interest from the mCMV IE2 promoter. Therefore, in a preferred embodiment, the vector comprises the mCMV IE2 promoter in combination with a second promoter, or a functional expression promoting fragment thereof. Examples for further suitable promoters include the hCMV promoter, the metallothoinein promoter (MT), the SV40 promoter, or artificial promoter. Preferably, the second promoter is a further copy of the mCMV IE2 promoter. Such further promoters may promote constitutive or regulated expression. Regulated expression may be inducible or repressible expression, or both.

Preferably, such second promoter is the promoter of the mCMV-IE1 gene, or a functional expression promoting fragment thereof. It is thus particularly preferred that the first promoter is the mCMV-IE2 promoter, or a functional expression promoting fragment thereof, and the second promoter is the mCMV-IE1 promoter, or a functional expression promoting fragment thereof.

The mCMV-IE1 promoter is known e.g. from WO 87/03905. It may comprise the core promoter containing the last 47 bp of the sequence of FIG. 1 (box), or additional 100 to 200 bp upstream sequences (i.e. the proximal promoter), or it may comprise the whole intergenic region up to position −1330 (relative to position +1 of the IE1, see FIG. 1).

In a preferred embodiment, the vector comprises a DNA sequence of SEQ ID NO: 1, including both the IE1 and the IE2 promoter as well as the IE 1 enhancer and the new IE2 enhancer, or any functional expression promoting fragment thereof.

In a highly preferred embodiment, in the vector according to the invention, the promoter, or a functional expression promoting fragment thereof, is operably linked to a DNA sequence coding for at least one polypeptide. In a further embodiment of the invention, the enhancer of the invention is present on the expression vector together with a DNA sequence coding for at least one polypeptide.

Preferably, the DNA sequence codes for a protein of interest.

It is further preferred that the DNA sequence codes for a marker protein, or is an amplifiable gene.

It is also preferred that the DNA sequence codes for a reporter protein.

Should the vector of the invention contain more than one promoter, any combination or sub-combination of protein of interest, marker, reporter, amplifiable gene, etc., may be expressed from the same plasmid, In accordance with the present invention, the polypeptide of interest may be any polypeptide which different from the IE2 polypeptide itself, be it an extracellular protein such as peptide hormones, cytokines or growth factors, or a transmembrane protein such as growth factor receptors or hormone receptors, or intracellular proteins such as kinases, phosphatases or DNA binding proteins, depending on the intended use of the polypeptide of interest or host cell in which it is expressed.

Marker proteins suitable in accordance with the present invention are e.g. negative or positive selection markers, or amplifiable genes. Examples include proteins selected from adenosine deaminase (ADA), aminoglycoside phosphotransferase (neo), dihydrofolate reductase (DHFR), hygromycin-B-phosphotransferase (HPH), thymidine kinase (tk), xanthine-guanine phosphoribosyltransferase (gpt), multiple drug resistance gene (MDR), ornithine decarboxylase (ODC) and N-(phosphonacetyl)-L-aspartate resistance (CAD), or puromycin acetyltransferase (PAC). Further examples include genes used for selection by use of particular metabolic pathways such as galactokinase (Schumperli et al., 1982), the folate receptor (Zhu et al., 2001), or reduced folate carrier (Assaraf et al., 1992).

In yet a further preferred embodiment the polypeptide of interest is a reporter gene.

The term "reporter gene" or "reporter protein", as used herein, is intended to mean a gene encoding a gene product that can be identified using simple, inexpensive methods or reagents, and that can be operably linked to a promoter region of the invention or an active fragment thereof. Reporter genes may be used to determine transcriptional activity in screening assays (see, for example, Goeddel (ed.), Methods Enzymol., Vol. 185, San Diego. Academic Press, Inc. (1990)), e.g. using Luciferase as reporter gene (Wood, 1991; Seliger and McElroy, 1960; de Wet et al. (1985), or commercially available from Promega®).

Examples are selected from luciferase, green fluorescent protein, alkaline phosphates, O-galactosidase, or horseradish peroxidase or intramolecular combinations with other proteins, such as e.g. the Green Fluorescent Protein (GFP) or enhanced GFP (EGFP) with the puromycin acetytransferase gene (Abbate et al., 2001), or combinations thereof.

Experimental data the present invention is based on showed that efficient simultaneous expression of polypeptides of interest may be achieved from the IE2 and IE1 promoter, both present on the same plasmid. Therefore, in a further preferred embodiment, both the mCMV IE2 promoter, and the mCMV-IE1 promoter, or the functional expression promoting fragments thereof, are operably linked to a polypeptide, respectively.

High expression levels may be achieved if both promoters are present in a bi-directional architecture. Therefore, the mCMV-IE2 promoter, or functional expression promoting fragment thereof, and a promoter, in particular the mCMV-IE1 promoter, or a functional expression promoting fragment thereof, are bi-directionally arranged.

The term "bi-directionally arranged", as used herein, is intended to mean that the promoters drive transcription in opposite directions. This arrangement of the plasmid DNA is also referred to as a "bi-directional architecture" of the vector.

The promoters of the mCMV-IE1 or mCMV-IE2 gene, or the functional expression promoting fragments thereof, or any further promoter that may be used in combination with the mCMV-IE2 promoter, or in combination with the IE2 enhancer, may further include a translation initiation signal.

In a further preferred embodiment, the promoter of the mCMV-IE2 gene, or a functional expression promoting fragment thereof, or the mCMV IE2 enhancer, is linked to other elements regulating or influencing transcription. Such elements may affect processing, stability or translation efficiency of RNA. Examples for suitable elements are selected from the group consisting of 5'UTRs, introns, 3'UTRs (see e.g. Mazumder et al, 2003), mRNA 3' end processing sequences (e.g. polyadenylation sites), and IRES sequences for polycistronic expression (see e.g. Mountford and Smith, 1995).

It is preferred to use an IRES element for expression of polycistronic mRNAs, in which the coding sequences are separated by the IRES. The advantage is that several polypeptides of interest may be expressed from the same mRNA and thus from the same promoter.

In yet a further preferred embodiment, the promoter of the mCMV-IE2 gene alone, or in combination with the promoter of the mCMV IE1 gene, or any other natural or artificial promoter, or the IE2 enhancer, may be linked to further expression promoting sequences such as insulators, boundary elements, LCRs (e.g. described by Blackwood and Kadonga (1998)) or matrix/scaffold attachment regions (e.g. described by Li et al., 1999).

The person skilled in the art may appreciate that the vector of the present invention may also contain further enhancers, such as e.g. the well known SV40 enhancer or the hCMV enhancer.

In accordance with the present invention, the polypeptide operably linked to a first promoter, preferably the mCMV IE 2 promoter, and the polypeptide operably linked to a second promoter, preferably the mCMV IE1 promoter, may be the same. In this case, two copies of the same gene are present on the same vector, but under the control of two different promoters. Thus, it may be possible to achieve an expression rate superior to expression from a single copy of a gene encoding a polypeptide of interest.

In an alternative embodiment, the polypeptide operably linked to a first promoter, preferably the mCMV IE2 promoter, and the polypeptide operably linked to a second promoter, preferably the mCMV IE1 promoter, are different. The invention thus provides for an efficient vector for co-expression of two different polypeptides, such as selection markers and proteins of interest, co-expression of two or more subunits of the same protein, or even of different domains of the same protein, should it be desirable to express them separately from each other, but in the same host cell.

The person skilled in the art will appreciate that several expression vectors in accordance with the present invention may be co-transfected into the same cell and serve for expression of multiple proteins and/or subunits of quite complex multimeric proteins.

It is preferred that the polypeptide operably linked to a first promoter, e.g. the mCMV IE2 promoter, is a first subunit of a dimeric or multimeric protein and the polypeptide operably linked to a second promoter, preferably the mCMV IE1 promoter, is a second subunit of a dimeric or multimeric protein. Co-expression of the two sub-units of a dimeric protein is preferred in accordance with the present invention. Co-expression of two subunits of the same protein is particularly advantageous since expression from both promoters may result in production of similar amounts of subunits, or of predetermined ratios of both polypeptides, depending on the strength of the promoters used. The subunits may then assemble in the same cell to form a mature protein.

Preferred examples for dimeric proteins suitable to be expressed using a vector of the invention are the alpha-chain and the beta-chain of a peptide hormone such as human FSH, human LH, human TSH and human CG. Either of the two subunits may be linked to a promoter in accordance with the invention, preferably the mCMV IE2 promoter. The person skilled in the art will appreciate that hormones from other species may be equally used in accordance with the present invention, such as equine, porcine, bovine hormones, for instance, depending on the intended use of the recombinant polypeptide.

In another embodiment of the invention, the first subunit is the heavy chain, and the second subunit is the light chain of an immunoglobulin, or vice versa. A preferred example of a suitable immunoglobulin is an IgG. Such immunoglobulins may e.g. be humanized or human antibodies for therapeutic use. A highly preferred example for such a humanized antibody is a humanized anti-CD11 antibody having the tradename Raptiva®.

Many polypeptides of interest may be expressed using a vector of the invention. In preferred embodiments, the polypeptide is selected from the group consisting of chorionic gonadotropin, follicle-stimulating hormone, lutropin-choriogonadotropic hormone, thyroid stimulating hormone, human growth hormone, interferons (e.g., interferon beta-1a, interferon beta-1b), interferon receptors (e.g., interferon gamma receptor), TNF receptors p55 and p65, interleukins (e.g., interleukin-2, interleukin-11), interleukin binding proteins (e.g., interleukin-18 binding protein), anti-CD11a antibodies, and muteins, fragments, soluble forms, functional derivatives, fusion proteins thereof.

Other preferred polypeptides of interest include, e.g., erythropoietin, granulocyte colony stimulating factor, granulocyte-macrophage colony-stimulating factor, pituitary peptide hormones, menopausal gonadotropin, insulin-like growth factors (e.g., somatomedin-C), keratinocyte growth factor, glial cell line-derived neurotrophic factor, thrombomodulin, basic fibroblast growth factor, insulin, Factor VIII, somatropin, bone morphogenetic protein-2, platelet-derived growth factor, hirudin, epoietin, recombinant LFA-3/IgG1 fusion protein, glucocerebrosidase, and muteins, fragments, soluble forms, functional derivatives, fusion proteins thereof.

The second aspect of the invention relates to a host cell transfected with at least one vector described above. The skilled person will appreciate that the host cell may equally be co-transfected with two or more vectors in accordance with the present invention.

Many host cells are suitable in accordance with the present invention, such as primary or established cell lines from a wide variety of eukaryotes including plant and animal cells, mammalian or human cells. For example, suitable host cells include CHO cells, COS cells, CV1 cells, mouse L cells, HT1080 cells, BHK-21 cells, HEK293 cells, NIH-3T3 cells, LM cells, Y1 cells, NS0 and SP2/0 mouse hybridoma cells and the like, Namalwa cells, RPMI-8226 cells, Vero cells, WI-38 cells, MRC-5 cells or other immortalized and/or transformed cells.

Preferably, the host cell is a CHO cell, and more preferably a CHO-S cell, described e.g. by Shotwell et al. (1982, J. Biol. Chem. 257:2974-2980). CHO cells were first cultured by Puck (J. Exp. Med. 108, 945, 1958) from a biopsy of an ovary from a female Chinese hamster. From these original cells a number of sub-lines were prepared with various characteristics. One of these CHO cell lines, CHO-K1, is proline-requiring and is diploid for the dihydrofolate reductase (DHFR) gene. Another line derived from this cell line is a DHFR deficient CHO cell line (CHO DUK B11) (PNAS 77, 1980, 4216-4220), which is characterized by the loss of DHFR function as a consequence of a mutation in one DHFR gene and the subsequent loss of the other gene.

All of these cells may be transfected with the vectors of the present invention, either transiently, or in a semi-stable (e.g., if vector is episomal) or stable (e.g. integrated into the genome) manner. Stable transfection is preferred in order to establish clones that continuously express the polypeptide of interest.

The IE2 promoter of the present invention, or the IE2 enhancer, may be used as regulatory elements in the frame of a technology called "Endogenous Gene Activation". The vector of the invention may comprise be introduced into the locus of the genome which is supposed to be activated by homologous recombination, thus operably linking the regulatory sequence (IE2 promoter and/or enhancer) with the gene of interest, the expression of which is required to be induced or enhanced. The technology is described e.g. in WO 91/09955.

In a third aspect, the invention relates to a process for the production of a polypeptide of interest comprising the step of transfecting a host cell with a vector according to the invention.

Depending on the nature of the polypeptide of interest, the process according to the invention leads to a secreted protein or polypeptide that may be harvested from the cell culture supernatant, or to a cell membrane protein or intracellular protein that may be isolated from the cells by known methods. The polypeptide produced in accordance with the present invention may serve any purpose, and preferably it is a therapeutic protein intended for administration to humans or animals.

Depending on the intended use, the cell itself having the polypeptide integrated may be the product of the process according to the invention. Such a cell may e.g. be used for cell-based therapy.

In a fourth aspect, the invention relates to a process for the production of a polypeptide of interest comprising the step of culturing a host cell in accordance with the invention.

In a preferred embodiment, the process further comprises the step of isolating the polypeptide of interest from the host cells or cell culture supernatant. This step is particularly advantageous and easy to carry out for secreted proteins that may be isolated simply from the cell culture supernatant. However, this step equally applies to isolating polypeptides from cellular membranes, or intracellular compartments, that may be isolated from host cells.

The process may be used in transient, stable, episomal or viral expression systems. As shown in the Examples below, the vector of the invention resulted in particularly strong expression of the desired protein if used in a stable expression system. Therefore, in a preferred embodiment the transfection is stable transfection.

In a fifth aspect, the vector according to the invention is used for expression of a gene of interest. Genes of interest may be e.g. the genes coding for any of the above-mentioned polypeptides of interest. The vector of the invention may also be used for expression of marker genes, reporter genes, amplifiable genes, or the like.

Preferably, the vector is used for simultaneous expression of two or more genes or cDNAs of interest. It may also be used for simultaneous expression of one gene of interest and one marker gene or reporter gene or amplifiable gene, or the like.

In the frame of the present invention, it has been surprisingly shown that a vector of the invention, in particular a vector comprising the IE2 promoter, the IE2 enhancer, and the IE1 promoter, resulted in the identification of clones that highly expressed a reporter gene and a gene of interest. Therefore, in a sixth aspect, the invention relates to the use of a vector according to the invention for selection of clones that express high amounts of a gene of interest.

In a seventh aspect, the invention relates to the use of a vector of the invention for the manufacture of a medicament for use in plasmid or DNA based therapy or gene therapy.

In an eighth aspect, the host cell of the invention is used for the manufacture of a medicament for cell-based therapy. Should the cell-based therapy be intended for human treatment, it is preferred that the host cell is a human cell or cell line, more preferably a cell or cell line derived from the patient that is to be treated.

Having now fully described this invention, it will be appreciated by those skilled in the art that the same can be performed within a wide range of equivalent parameters, concentrations and conditions without departing from the spirit and scope of the invention and without undue experimentation.

While this invention has been described in connection with specific embodiments thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

EXAMPLES

Example 1

Evaluation of Expression Vectors in Transient Transfections

Materials and Methods:

Materials

Cells: CHO-S, origin Gibco/Invitrogen (Cat no 11619).

Plasmid DNAs constructed as depicted in FIGS. 2 and 3 were isolated from overnight growing standard cultures with the Nucleobond PC 500 kit (Macherey-Nagel Cat. No 740 574) according to the manufacturer's protocol.

Transfection:

Lipofectamine (Invitrogen, Cat No 18324-012)

Format: 24 well plates.

Cells: CHO-S cells in exponential growth phase were passaged 24 h before transfection. To avoid a stationary phase at low cell density, the cells were diluted to $0.75 \times 10^6$ cells/ml. The total amount of cells to be transfected was $1.5 \times 10^5$, resuspended in 100 µl serum free medium SFM II (Invitrogen, Cat No 12052-114) per well, in 24 well plates.

Transfection mixes were as follows:

A) Lipofectamine: 2 µl
SFM II Medium: 48 µl
Total volume is 50 µl

B) DNAs: 1 µg (50 ng expression vector+950 ng carrier plasmid, pBluescript II KS (+), Stratagene, cat. 212205-01
SFM II Medium: complement to 50 µl.

Solutions A and B were mixed, and incubated for 30 min at room temperature.

This mix was added to the 100 µl SFM II Medium containing $1.5 \times 10^5$ cells. The cells were placed back to the incubator and incubated for 37° C., 5% $CO_2$ for 3 hours. Then, 400 µl SFM II Medium were added in order to dilute the Lipofectamine. Then, the cells were incubated for another 48 hours before sampling for analysis. All transfections were carried out in triplicate.

Luciferase Measurement:

The Bright-Glo Luciferase assay system from Promega, Cat No E2610 was used for Luciferase measurement according to the manufacturer's guidelines.

Briefly, the cell suspension was homogenized by pipetting up and down several times, and an aliquot of 50 µl was taken out and put it in a white 96 well plate (Nunc, Cat no 236108). Then, 50 µl of reconstituted Bright-Glo Reagent was added and incubated for 5 min at room temperature. Light emission was measured on a Centro LB 960 luminometer (Berthold Technologies) during 5 seconds of acquisition time.

Results

The expression vector constructs that were used in a CHO-S cell based transient expression system are depicted in FIG. 2. In this series of experiments, Luciferase was used as a reporter gene for evaluation of gene expression. Vectors having either no promoter at all (construct A) or the SV40 promoter/enhancer (construct B), which is not highly active in CHO-S cells, were used as controls.

The results from transient transfection experiments with vectors A to G are shown in FIG. 4. In constructs C and F, Luciferase expression is driven by the IE1 promoter. Both constructs resulted in Luciferase expression. Construct C further contained the IE2 promoter arranged bidirectionally with regard to the IE1 promoter. This bi-directional arrangement reduced the expression efficiency from the IE1 promoter, construct C, as compared to the use of IE1 promoter alone, construct F. A short version of 0.68 kb of the IE1 promoter (construct G) was less efficient than the longer version (construct F).

Irrespective of the presence or absence of a second promoter in the same construct, the IE2 promoter efficiently drove Luciferase expression (constructs D and E) and may thus be used as a promoter element in expression vectors for expression of polypeptides of interest.

In contrast to the IE1 promoter, the IE2 promoter was less efficient if used alone (construct E) than if used in a bi-directional architecture (construct D). It is therefore particularly suitable for use in bi-directional expression vectors.

Example 2

Evaluation of Expression Vectors in Stable Transfection

Materials and Methods

Methods:

Cells: CHO-S, from Gibco/Invitrogen (Cat no 11619).

Plasmid DNAs (according to FIG. 2) were isolated from overnight growing standard cultures with the Nucleobond PC 500 kit (Macherey-Nagel Cat. No 740 574) according to the protocol provided by the manufacturer.

Transfection:

Lipofectamine (Invitrogen, Cat No 18324-012)

For stable transfections, T75 flasks were used. CHO-S in exponential growth phase were passaged 24 h before transfection. To avoid a stationary phase at low cell density, they were diluted to $0.75 \times 10^6$ cells/ml. The total amount of cells to be transfected was $5 \times 10^6$, resuspended in 7 ml SFM II medium (Invitrogen Cat no 12052-114) in a T75 flask.

Transfection mixes were as follows:

A) Lipofectamine: 52.1 µl
SFM II Medium: 517.9 µl
Total volume is 570 µl.

B) DNAs: 10 µg linearised plasmid DNA, (9 µg Luc expression vector+1 µg plasmid for selection: SV40 promoter driving Puromycine resistance gene. All plasmids were linearised with PvuI)

SFM II Medium was complemented to 570 µl.

A and B were mixed and incubated for 30 min at room temperature. 7 ml containing $5 \times 10^6$ cells were added and the cells placed back in an incubator at 37° C. and 5% $CO_2$ for 3 hours. Then the culture was centrifuged at 800 g for 3 minutes, and the cell pellet resuspended in 5 ml EX-CELL 325 (JRH, Cat no 14335-1000M), supplemented with 1×HT and 4.5 mM L-Glutamine (100×HT, Invitrogen, Cat. no 11067-030, L-Glutamine 200 mM, Sigma, G-7513). 5 ml EX-CELL 325 were added directly to the T75 flask in order to resuspend adhering cells, and added to the suspension. In total, $5 \times 10^6$ cells were in 10 ml EX-CELL 325 medium.

Selection Procedure:

Selection was applied 48 hours post transfection by exchanging the medium and diluting to $1 \times 10^6$ cells/ml in EX-CELL 325 containing 10 µg/ml puromycine (Sigma, P-8833). Every two days, cells were counted, centrifuged, and resuspended in fresh selective medium at $1 \times 10^6$ living cells/ml. Viability was checked at these points. After 21 to 35 days the selection was completed, and cell viability was higher than 80%.

Luciferase Measurement:

Two hours before sampling the culture, the cells were counted and the culture diluted to $0.2 \times 10^6$ living cells/ml.

The Bright-Glo Luciferase assay system from Promega, Cat No E2610 was performed according to the manufacturer's guidelines.

Briefly, the cells were suspended by pipetting up and down several times, and an aliquot of 50 µl was taken out and put in a white 96 well plate (Nunc, Cat no 236108). 50 µl of reconstituted Bright-Glo Reagent was directly added, and incubated for 5 min at room temperature. Light emission was measured on a Centro LB 960 luminometer (Berthold Technologies) during 5 seconds of acquisition time.

Luciferase activity was then normalized by the number of living cells in the sample tested, i.e. typically $1\times10^4$ cells.

Results

Constructs C, D, E and F (see FIG. 2) were tested in a stable expression system. The results are depicted in FIG. 5. Construct E, comprising the IE2 promoter alone, resulted in the strongest expression of luciferase in this system. If present together with the IE1 promoter in bi-directional arrangement (construct D), the IE2 promoter still resulted in luciferase expression that was superior to expression driven by the IE1 promoter, either alone (construct F) or in bi-directional arrangement with the IE2 promoter (construct C).

Example 3

Co-Expression of Two Polypeptides of Interest from Bi-Directional Expression Vectors Materials and Methods:

The transfections were carried out as described in Examples 1 and 2. Briefly, CHO-S cells (in suspension, Gibco SFMII) were transiently transfected with 900, 500, 300 and 100 ng of vector DNA (construct C-2, see FIG. 3) in 24 well plates (triplicates for each condition). Two days post transfection, luciferase assays were carried out with cell extracts from the triplicates as expressed by RLU (relative light units). Supernatants from the same wells were taken before cell lysis, pooled and assayed for IL18BP by Elisa (see below).

IL-18BP ELISA

The amount of recombinant human IL-18BP (rhIL-18BP) in the supernatant was measured by standard ELISA using a proteinG-purified monoclonal anti-rh-IL-18BP antibody that was coupled to biotin. Extravidine-HRP (Sigma) was used as detection reagent.

FIG. 9 shows the amounts of IL-18 BP in ng/ml and luciferase in RLU expressed by 48 clones at day 90 after stable transfection with a bi-directional mCMV promoter construct (see FIG. 3). The detection limit for luciferase was about 500 RLU, and 2.5 ng/ml for IL-18BP.

Results

In this series of experiments, concomitant expression of two genes from construct C-2, depicted in FIG. 3, was assayed. The marker gene (Luciferase) was expressed from the IE1 promoter, and the gene of interest, the IL-18BP gene, was expressed from the IE2 promoter. IL-18BP is a secreted protein. The promoters were arranged in bi-directional architecture, i.e. both promoters simultaneously drove expression in opposite directions.

The results of this study are depicted in FIGS. 6 to 9. FIG. 6 shows the extent of luciferase expression as expressed by RLU measured in a transient expression system. In the same transient expression system, IL-18BP was measured by ELISA in the cell culture supernatants. FIG. 7 shows the results in ng/ml of secreted IL-18BP. FIG. 8 shows the ratios of IL-18BP to Luciferase in each transient expression experiment.

As shown in FIGS. 6 to 8, different amounts of plasmid DNA were used for transfection. All amounts of DNA used resulted in expression of both Luciferase and IL-18BP. Surprisingly, the best results were obtained with the lowest amount of DNA transfected, 100 ng of vector DNA, consistently for IL-18BP and luciferase.

Furthermore, the stable quotient (FIG. 8) indicates a constant relationship between the expression potential of both promoters.

In conclusion, these data demonstrate that both genes are simultaneously expressed from the two promoter units, further showing that both expression units are fully functional in the bi-directional promoter architecture.

Then, construct C-2 was stably transfected, and the expression of Luciferase and IL18BP assayed in 48 independent clones.

Stable transfections were carried out according to the protocol described in example 2, with the exception that the medium used after transfection was ProCho5 (Cambrex, cat. 12766Q).

For single cell cloning, the pool was arrayed in 384 well plate (Nunc, cat. 164688) at a density of 0.5 cell per well (70 µl/well) using a Multidrop dispenser (ThermoLabsystems, cat. 5840150). 8 days later, 192 clones were randomly picked and analyzed for Luciferase expression. 48 clones with highest Luc expression were chosen and re-assayed for both Luciferase (luminometry) and IL18 BP expression (by manual ELISA, see above).

FIG. 9 shows the results of this experiment. All 48 clones expressed Luciferase and IL-18BP, albeit in varying amounts.

Example 4

Minimal Enhancer Sequence Definition

Materials and Methods
Plasmid DNAs

A set of vectors containing shortened mCMV promoters were built using PCR (Polymerase Chain Reaction) and specific primers matching along the mCMVp (Table 1).

PCR conditions were as follows:
Mix:
10 ng DNA plasmid (prevmCMV-Luciferase (ΔXhoI), construct E of FIG. 2)
50 pmol of both sense and antisense primer (see table 1 below, common antisense for all)
200 µM each dNTPs (dATP, dTTP, dGTP, dCTP)
1× Dynazyme buffer, containing 1.5 mM $MgCl_2$)
4 units of Dynazyme II DNA polymerase (Finnzymes, cat. F-501S)
Cycling parameters:
95° C., 5'
2 cycles:
95° C., 30"
52° C., 30"
72° C., 1'30
2 cycles:
95° C., 30"
54° C., 30"
72° C., 1'30
10 cycles:
95° C., 30"
58° C., 30"
72° C., 1'30
15 cycles:
95° C., 30"
60° C., 30"
72° C., 1'30

5 µl of each PCR reaction was loaded on a 1% agarose gel. Bands having the correct length were cut out and purified using Qiagen Minilute Gel Extraction kit, cat. 28606, prior to cloning.

TABLE 1

| Position | Primer |
|---|---|
| −1076 | CCGCTCGAGACCTTATGTACGTGCCA (SEQ ID NO: 3) |
| −783 | CCGCTCGAGCTCCAATGGAACTTTCCTG (SEQ ID NO: 4) |
| −587 | CCGCTCGAGACTTTCCTGTTGATTCACC (SEQ ID NO: 5) |
| −387 | CCGCTCGAGCAAAACCCAGTGGAAAGTC (SEQ ID NO: 6) |
| −189 | CCGCTCGAGATGCCATATGAGTGTATTAG (SEQ ID NO: 7) |
| E1-IE2as | CGGAATTCGATATCCGCGGCTCTC (SEQ ID NO: 8) |

The positions corresponding to the number of base pairs kept from mCMVp, considering the +1 from IE2 as reference, are: −1076, −783, −587, −387 and −189

The cloning strategy for any of the promoter fragments was the same, PCRs were carried out on full length mCMVp (prevmCMV-Luciferase (ΔXhoI), i.e. construct E of FIG. 2). The fragments were then digested by XhoI/EcoRI, two restriction sites added at the extremity of the specific primer sequence. The promoter sequence was then removed from construct E by digesting it by XhoI/EcoRI, and shorter versions were inserted at the very same locus.

The evaluation of the constructs was done by transient Lipofectamine transfection followed by Luciferase measurement. Further materials and methods were as described in Example 1. The SFM medium used in this example was ProCho5, Cambrex, B-12766Q.

Results

Vectors H to N (FIG. 10.a) comprising the mCMV IE2 promoter driving the Luciferase gene were constructed in order to define minimal sequences required for high expression levels from the IE2 promoter.

The seven expression vector constructs H to N were used in a CHO-S cell based transient expression system. The results are depicted in FIG. 10.b). Construct L is the shortest construct retaining strong expression of Luciferase in this system. Construct M still resulted in Luciferase expression the level of which was about 30% of the expression level reached with constructs H to L. Luciferase expression obtained with construct N was very low but still significant, indicative of basal promoter activity as expected for a productive transcription start site containing a TATA box and initiator.

In conclusion, these experiments define a new enhancer in the mCMV IE2 upstream region, herein called mCMV IE2 enhancer. In the above experiments, the IE2 enhancer increases transcription from the minimal IE2 promoter retained in construct N. The minimal sequence required for high reporter gene expression is within the −587 to −189 bp fragment (construct L), and a construct comprising the −387 to −189 bp fragment still enhanced Luciferase expression (construct M).

Example 5

The New IE2 Enhancer Activates a SV40 Minimal Promoter

Further experiments were carried out in order to assess whether the new IE2 enhancer indeed fulfills all criteria required for enhancer activity, i.e. enhancing expression independently from (1) location, (2) orientation, and (3) promoter identity. In order to do so, constructs O to V were constructed in order to assess that the new IE2 enhancer could enhance expression of an heterologous promoter, the SV40 promoter, independently of the orientation, distance and position (5' or 3'), relative to the SV40 promoter. Constructs W, X and Y were the controls, W containing the SV40 enhancer, X not containing any enhancer, but the SV40 promoter, and Y containing neither an enhancer nor a promoter.

Vector Construction

A vector called pSV-Luc (construct X of FIG. 11(a)) which contains only the SV40 promoter was constructed from pGL3-Ctrl (Promega, E 1741), containing SV40 promoter driving Luciferase gene, and SV40 enhancer located in 3' of the gene (construct W), and pGL3-Basic (Promega, E1751), lacking both promoter and enhancer (construct Y).

Briefly, pGL3-ctrl was cut with NotI/XbaI to isolate a fragment containing the SV40 promoter, followed by the Luciferase gene. In a similar way, pGL3-basic was cut with NotI/XbaI and the vector backbone containing the poly A region was isolated, without the 3' enhancer. By combining the two fragments, pSV-Luc (construct X) was obtained.

The region 5' of the SV40 promoter of this vector was engineered by cloning the IE2 enhancer sequence (−587 to −189) in both orientations, called p5' enh-SV-Luc (construct O), and p5' reverse enh-SV.Luc (construct Q). Furthermore, the IE2 enhancer sequence (−587 to −189) was also cloned into the 3' region of the Luciferase gene, in both orientations. Resulting vectors were called p3' enh-SV-Luc+ (construct S), and p3' reverseenh-SV.Luc. (construct U), The same procedure was carried out with the short version of the IE2 enhancer, i.e. having −387 to −189 instead of −587 to −189, and were called constructs P, R, T and V, see FIG. 11.a.

Construct O, P: Recipient vector was pSV-Luc+ (construct X of FIG. 11.a) opened by digestion with NheI/SmaI. The full-length enhancer was isolated by a digestion with NdeI, followed by blunt-ending reaction using Klenow polymerase, purification and digestion by NheI. The same strategy was applied for construction of the short enhancer construct.

Construct Q, R: Recipient vector was pSV-Luc+ (construct X of FIG. 11.a) opened by digestion with XhoI/SmaI. The full-length enhancer was isolated by a digestion with NdeI, followed by blunt.ending reaction using klenow polymerase, purification and digestion by XhoI. The same strategy was applied for construction of the short enhancer construct.

Construct S, T, U and V: Recipient vector is pSV-Luc+ (construct X of FIG. 11.a) opened by digestion with BamHI, followed by blunt ending using Klenow polymerase. The full-length enhancer was isolated by a digestion with NdeI/NheI, followed by blunt.ending reaction using Klenow polymerase. Cloning allowed both orientations which was identified by restriction analysis. Both orientations were kept for analysis The same strategy was applied for construction of the short enhancer construct.

Constructs pGL3-Basic (construct Y) served as no expression control. pGL3-ctrl (construct W) served as SV40 promoter/enhancer vector. pSV-Luc was the control having the SV40 promoter alone (construct X).

Transfections and Luciferase measurements were carried out as in the previous examples.

Results

The results obtained with constructs O to Y of FIG. 11.*a* are depicted in FIG. 11.*b*. The enhancer-less SV40 promoter construct was taken as a baseline for added enhancer activity, and the activity measured with construct X was set as 1. All constructs having either the long or the short IE2 enhancer resulted in expression of the reporter gene. The long version consistently resulted in high expression of the reporter gene from the SV40 promoter, which was much higher that the expression level obtained with the combination of the SV40 promoter and SV40 enhancer (construct O). Therefore, this experiment clearly defines the −587 to −189 sequence and the −387 to −189 sequence as bona fide enhancers, activating a heterologous promoter in a position- and orientation independent manner.

Example 6

Comparison Between the Long IE2 Enhancer Version (−587 to −189) and the hCMV Enhancer Experimental protocols for transfection with Lipofectamine, followed by Luciferase measurement, are described in Example 1.

Results

In this experiment, constructs O and Q, having the long version of the new IE2 enhancer in both orientations in 5' of the SV40 promoter, were used for comparison to a known strong enhancer, the hCMV (human cytomegalovirus) enhancer. To this end, the mCMV IE2 sequence was replaced by the hCMV enhancer sequence (SEQ ID NO: 2) in construct O, resulting in construct O-2. The same was done in construct Q, resulting in construct Q-2.

The hCMV enhancer sequence having MluI sites (MluI=acgcgt) flanking it, which were used for cloning, was as follows:

```
                                              (SEQ ID NO: 2)
aCGCGTTGACATTGATTATTGACTAGTTATTAATAGTAATCAATTACGGG

GTCATTAGTTCATAGCCCATATATGGAGTTCCGCGTTACATAACTTACGG

TAAATGGCCCGCCTGGCTGACCGCCCAACGACCCCCGCCCATTGACGTCA

ATAATGACGTATGTTCCCATAGTAACGCCAATAGGGACTTTCCATTGACG

TCAATGGGTGGACTATTTACGGTAAACTGCCCACTTGGCAGTACATCAAG

TGTATCATATGCCAAGTACGCCCCCTATTGACGTCAATGACGGTAAATGG

CCCGCCTGGCATTATGCCCAGTACATGACCTTATGGGACTTTCCTACTTG

GCAGTACATCTACGTATTAGTCATCGCTATTACCATGGTGATGCGGTTTT

GGCAGTACATCAATGGGCGTGGATAGCGGTTTGACTCACGGGGATTTCCA

AGTCTCCACCCCATTGACGTCAATGGGAGTTTGTTTTGGCACCAAAATCA

ACGGGACTTTCCAAAATGTCGTAACAACTCCGCCCCACGCGTGCTAGCCC

GGGCTCGAGATCTGCGATCTGCATCTCAATTAGTCAGCAACCATAGTCCC

GCCCCTAACTCCGCCCATCCCGCCCCTAACTCCGCCCacgcgt.
```

SV-Luc+ was digested with MluI, and treated by Calf Intestine Alkaline Phosphatase to prevent self ligation. The hCMV promoter sequence was cloned in MluI site. Both orientation clones were kept for comparison with equivalent IE2 constructs.

Results of Luciferase expression are shown in FIG. 12. The Luciferase expression level obtained with the new IE2 enhancer (long version) were at least twice as high as the Luciferase expression levels obtained with the classical hCMV enhancer.

Example 7

IE2 Enhancer Performance in a Bi-Directional Construct

Two further constructs were designed to test the new enhancer in a bi-directional architecture, called constructs #26 and #140 as depicted in FIG. 13.

26: The basis of this vector was mCMV-Luc+ (construct C, FIG. 3). It was digested with SacII/EcoRI. The IL-18BP cassette was taken from phCMV-IL18BP2. By cutting this vector with SacII/EcoRI, a fragment containing the Intron A followed by IL-18BP open reading frame and the SV40polyA region was isolated.

140. The basis of this vector was construct L of FIG. 10.*a*. It was digested with XhoI/NheI, opening the vector 5' of the IE2 enhancer. A vector expressing IL18BP from IE1promoter, called pBS.I IL18BP(IE1).I, was used as insert donor. By digesting this vector with XhoI/SpeI, a fragment was isolated containing the IE1 promoter from XhoI (see FIG. 1) followed by the IntronA-IL18BP-SV40polyA cassette. The resulting construct lacked the sequence between −589 to XhoI of the original mCMV promoter sequence.

Stable transfections and Luciferase measurement were carried out as described in example 2, and the IL18BP ELISA as described in example 3.

However, construct #140 does not exactly mirror construct #26 in that the IE1 and IE2 promoters are in reverse orientation. Thus, Luciferase expression was driven by the IE1 promoter in construct #26, but by the IE2 promoter in construct #140, and IL18BP expression was driven by the IE2 promoter in construct #26 and by the IE1 promoter in construct #140.

The results obtained with both constructs are shown below, since they are significant for the simultaneous effect of the new IE2 enhancer on two different promoters in a bi-directional expression vector (construct #140).

FIG. 14 depicts the results from pools stably transfected with construct #26 and #140 in terms of Luciferase and IL-18BP expression. Construct #140 resulted in higher expression of both marker gene (Luciferase) and gene of interest (IL-18BP).

In order to assess stability of expression of Luciferase and IL-18BP, the pools were either kept under selective conditions, i.e. under puromycin treatment, or were kept without selective pressure (without puromycin) for three weeks. The results are shown in FIGS. 15 to 17. The expression levels of the reporter gene Luciferase and the IL-18BP did not significantly change over time, see FIGS. 16 and 17.

Thus, it was demonstrated that both constructs #26 and #140 showed similar expression levels over time, in presence or absence of selection pressure. Therefore, constructs having the new IE2 enhancer are suitable for stable and simultaneous expression of two genes.

As the above results were obtained in pools, clones were derived by limiting dilution at 0.5 cells well from both pools.

Clones were cultivated under puromycin selection, in order to evaluate clonal expression levels. Then, the isolated clones were split in presence and absence of puromycin to eventually monitor their stability. The results presented in FIGS. 18 and 19 were taken before the clones were split in +/− puromycin conditions. Results from 2 weeks after removal of puromycin showed no significant difference for both constructs, thus suggesting stability. This study will be continued for another 10-12 weeks.

In order to evaluate expression of both genes a high throughput format was used, namely in 96 well plates:

Day 1: Dilution ½ of the cells, 100 µl of ProCho5 culture medium (serum free)+100 µl of fresh ProCho5 containing 5% Fetal Bovine Serum. With 2.5% FBS final concentration, cells were able to attach. Weekly passage of the maintenance plate was done in a ¹/20 dilution factor, all in ProCho5 medium.

Day 2: Medium was discarded, washed once with 200 µl 1×PBS (Invitrogen, 10010-015), and 75 µl fresh ProCho5 containing 5% FBS added, and incubated for a 24 h expression pulse.

Day 3: 50 µl of the supernatants were recovered, and 200 µl Elisa buffer added (1×PBS, 0.1% w/v BSA, 0.2% v/v Tween 20). 100 µl were analyzed by ELISA for IL-18BP.

The wells were washed with 200 µl 1×PBS (discard) and 100 Glo Lysis buffer (Promega, E266a) were added. The wells were incubated for 30 min at room temperature to ensure cell lysis. Luciferase measurement was done using 30 µl lysed cells transferred in a white 96 well plate+30 µl reconstituted Bright-Glo reagent. Light emission was measured on a Centro LB960 luminometer during 5 seconds acquisition time.

The analyses of the clones obtained from stable transfections with construct #26 are depicted in FIG. 18, and the ones resulting from stable transfection with construct #140 in FIG. 19.

The clones depicted in FIGS. 18 and 19 were ranked by their Luciferase value in a descending manner. IL18BP expression was indicated as OD value. Since the Elisa was carried out in high throughput format, real quantification of the IL-18BP levels could not be obtained. However, controls at 2500 ng/ml and 250 ng/ml as well as blank were included to monitor plate to plate variation.

FIG. 20 shows luciferase expression on the plates in inverted ChemiDoc view. This view uses a CCD camera (Biorad), allowing to acquire signals coming from chemiluminescence (as in FIG. 20). A Software called Quantity One 4.2.3 allows picture management like inverting the signals, which was employed here.

As evident from the results shown in FIGS. 18 to 20, construct #140 resulted in a lot of non-expressing clones. However, surprisingly, the few positive clones expressed both genes extremely strongly.

Therefore, construct #140 allows screening for very high expressors in very early cloning phases, thus omitting the necessity to test and follow-up on high numbers of clones in order to identify the few clones that highly express both genes of interest.

REFERENCES

1. Abbate et al., Biotechniques 2001 August; 31(2):336-40
2. Assaraf et al., J Biol Chem 1992 Mar. 25; 267(9):5776-84
3. Blackwood E M, Kadonaga J T. Science 1998 Jul. 3; 281(5373):61-3
4. De Wet et al. (1985) Proc. Natl. Acad. Sci. USA 82, 7870
5. Dorsch-Haesler, K. et al. (1985). Proc. Natl. Acad. Sci. USA 82:8325-8329
6. Goeddel Methods Enzymol., Vol. 185, San Diego
7. Li Q, Harju S, Peterson K R. Trends Genet. 1999 October; 15(10):403-8
8. Manning W C and Mocarski, E S, Virology 167, 477-484 (1988).
9. Mazumder B, Seshadri V, Fox P L. Trends Biochem Sci 2003 February; 28(2):91-8
10. Messerle, M. et al. (1991). J. Virol. 65:1638-1643
11. Kim, S-Y. et al. (2002). J. Biotech. 93:183-187.
12. Mountford P S, Smith A G. Trends Genet. 1995 May; 11(5):179-84.
13. Sandford and Burns, Virology 222, 310-317 (1996)
14. Schumperli et al., Proc Natl Acad Sci USA 1982 January; 79(2):257-61
15. Seliger and McElroy (1960) Arch. Biochem. Biophys. 88, 136
16. Shotwell et al., 1982, J. B. C. 257(6), 2974-80
17. Wood et al., (1991) Biochem. Biophys. Res. Comm. 124, 592.
18. U.S. Pat. No. 4,963,481.
19. U.S. Pat. No. 4,968,615
20. Zhu et al., J Cell Biochem 2001 Mar. 26; 81(2):205-19

We claim:

1. An expression vector comprising a mCMV-IE2 promoter fragment consisting of nucleotides 1 to 39 of SEQ ID NO: 1 directly linked to a DNA sequence encoding a heterologous polypeptide.

2. The vector according to claim 1, wherein said vector further comprises a mCMV-IE2 enhancer comprising SEQ ID NO: 9.

3. The vector according to claim 2, wherein said mCMV-IE2 enhancer comprises SEQ ID NO: 10.

4. The vector according to claim 1, further comprising a second promoter different from said mCMV-IE2 promoter.

5. The vector according to claim 4, wherein the second promoter is the mCMV-IE1 promoter.

6. The vector according to claim 4, wherein the mCMV-IE2 promoter fragment and the second promoter are bi-directionally arranged.

7. The vector according to claim 4, further comprising one or more regulatory elements selected from a 5'UTR, an intron, a 3'UTR, a mRNA 3' end processing sequence, a polyadenylation site, or an internal ribosome entry sequence (IRES).

8. The vector according to claim 7, wherein the IRES is operably linked to a DNA sequence encoding at least one polycistronic mRNA.

9. The vector according to claim 7, further comprising one or more DNA element selected from an insulator, a boundary element, a locus control region (LCR), a matrix attachment region (MARs), an element for recombination or an element for cassette exchange.

10. A host cell transfected with the vector according to claim 1.

11. The host cell according to claim 10, wherein the host cell is a CHO cell.

12. A process for the production of a polypeptide comprising the step of transfecting a host cell according to claim 10 and culturing said host cell under conditions allowing expression of the polypeptide.

13. The process according to claim 12, wherein the transfection is a stable transfection.

14. The process according to claim 13, further comprising the step of isolating the polypeptide from the host cell or cell culture supernatant.

15. The process according to claim 12, further comprising the step of isolating the polypeptide from the host cell or cell culture supernatant.

16. The vector according to claim 1, wherein said expression vector further comprises a second promoter directly linked to a DNA sequence encoding a second polypeptide.

17. A host cell comprising an expression vector according to claim 16.

18. The vector according to claim 16, wherein the second promoter is different from said mCMV-IE2 promoter.

19. The vector according to claim 16, wherein the second promoter is the mCMV-IE1 promoter.

20. The vector according to claim 16, wherein the heterologous polypeptide or the second polypeptide is a marker protein.

21. The vector according to claim 20, wherein the marker protein is selected from an adenosine deaminase (ADA), an aminoglycoside phosphotransferase (neo), a dihydrofolate reductase (DHFR), a hygromycin-B-phosphotransferase (HPH), a thymidine kinase (tk), a xanthine-guanine phosphoribosyltransferase (gpt), a multiple drug resistance gene (MDR), an ornithine decarboxylase (ODC), carbamyl-P synthetase/aspartate transcarbamylase/dihydro-orotase, a puromycin acetyltransferase (PAC), a galactokinase, a human folate receptor, or a reduced folate carrier.

22. The vector according to claim 16, wherein the heterologous polypeptide or the second polypeptide is a reporter protein.

23. The vector according to claim 22, wherein the reporter protein is selected from a luciferase, a green fluorescent protein, an alkaline phosphatase, and a horseradish peroxidase or combinations thereof.

24. The vector according to claim 16, wherein the heterologous polypeptide and the second polypeptide are the same.

25. The vector according to claim 16, wherein the heterologous polypeptide and the second polypeptide are different.

26. The vector according to claim 25, wherein the heterologous polypeptide is a first subunit of a dimeric or a multimeric protein and the second polypeptide is a second subunit of a dimeric or a multimeric protein.

27. The vector according to claim 26, wherein the first and the second subunit comprise the alpha and the beta chain of a hormone selected from a human FSH, a human LH, a human TSH or a human CG.

28. The vector according to claim 26, wherein one subunit is a heavy chain and the other subunit is a light chain of an immunoglobulin.

* * * * *

UNITED STATES PATENT AND TRADEMARK OFFICE
CERTIFICATE OF CORRECTION

PATENT NO.        : 9,051,582 B2
APPLICATION NO.   : 12/872151
DATED             : June 9, 2015
INVENTOR(S)       : Philippe Chatellard and Markus Imhof Page 1 of 1

It is certified that error appears in the above-identified patent and that said Letters Patent is hereby corrected as shown below:

In the specification

Column 14,
Line 50, "1×HT" should read --1X HT--.
Line 51, "(100×HT," should read --(100X HT,--.

Column 16,
Line 47, "1×" should read --1X--.

Signed and Sealed this
Twenty-second Day of December, 2015

Michelle K. Lee
*Director of the United States Patent and Trademark Office*

SEQUENCE LISTING

```
<160> NUMBER OF SEQ ID NOS: 10

<210> SEQ ID NO 1
<211> LENGTH: 1394
<212> TYPE: DNA
<213> ORGANISM: Artificial sequence
<220> FEATURE:
<223> OTHER INFORMATION: murine cytomegalovirus immediate early (mCMV
      IE) region

<400> SEQUENCE: 1
ctctgggctc gaatggcatg ggggacagct tttatatggt taactccgcc cgttttatga      60
ctagaaccaa tagtttttaa tgccaaatgc actgaaatcc cctaatttgc aaagccaaac    120
gccccctatg tgagtaatac ggggactttt tacccaattt cccaagcgga aagcccccta    180
atacactcat atggcatatg aatcagcacg gtcatgcact ctaatggcgg cccataggga    240 cttttccacat aggggggcgtt caccatttcc cagcataggg gtggtgactc aatggccttt    300
acccaagtac attgggtcaa tgggaggtaa gccaatgggt ttttcccatt actggcaagc    360
```

```
acactgagtc aaatgggact ttccactggg ttttgcccaa gtacattggg tcaatgggag      420
gtgagccaat gggaaaaacc cattgctgcc aagtacactg actcaatagg gactttccaa      480 tgggttttc cattgttggc aagcatataa ggtcaatgtg ggtgagtcaa tagggacttt       540
ccattgtatt ctgcccagta cataaggtca ataggggtg aatcaacagg aaagtcccat       600
tggagccaag tacactgcgt caatagggac tttccattgg gttttgccca gtacataagg      660 tcaataggg atgagtcaat gggaaaaacc cattggagcc aagtacactg actcaatagg       720
gactttccat tgggttttgc ccagtacata gggtcaatag gggtgagtc aacaggaaag       780 ttccattgga gccaagtaca ttgagtcaat agggactttc caatgggttt tgcccagtac      840
ataaggtcaa tgggaggtaa gccaatgggt ttttcccatt actggcacgt atactgagtc      900
attagggact ttccaatggg ttttgcccag tacataaggt caataggggt gaatcaacag      960
gaaagtccca ttggagccaa gtacactgag tcaataggga cttccattgg gttttgccc      1020 agtacaaaag gtcaataggg ggtgagtcaa tgggtttttc ccattattgg cacgtacata     1080
aggtcaatag gggtgagtca ttgggttttt ccagccaatt taattaaaac gccatgtact     1140 ttccaccat tgacgtcaat gggctattga aactaatgca acgtgacctt taaacggtac      1200
tttcccatag ctgattaatg ggaaagtacc gttctcgagc caatacacgt caatgggaag     1260
tgaaagggca gccaaaacgt aacaccgccc cggttttccc ctggaaattc catattggca     1320
cgcattctat tggctgagct gcgttctacg tgggtataag aggcgcgacc agcgtcggta     1380
ccgtcgcagt cttg                                                      1394
```

<210> SEQ ID NO 2
<211> LENGTH: 644
<212> TYPE: DNA
<213> ORGANISM: Artificial sequence
<220> FEATURE:
<223> OTHER INFORMATION: human cytomegalovirus enhancer

<400> SEQUENCE: 2

```
acgcgttgac attgattatt gactagttat taatagtaat caattacggg gtcattagtt       60
catagcccat atatggagtt ccgcgttaca taacttacgg taaatggccc gcctggctga      120
ccgcccaacg acccccgccc attgacgtca ataatgacgt atgttcccat agtaacgcca      180
atagggactt tccattgacg tcaatgggtg gactatttac ggtaaactgc ccacttggca      240
gtacatcaag tgtatcatat gccaagtacg ccccctattg acgtcaatga cggtaaatgg      300
cccgcctggc attatgccca gtacatgacc ttatgggact ttcctacttg gcagtacatc      360
tacgtattag tcatcgctat taccatggtg atgcggtttt ggcagtacat caatgggcgt      420
ggatagcggt ttgactcacg gggatttcca agtctccacc ccattgacgt caatgggagt      480
ttgttttggc accaaaatca acgggacttt ccaaaatgtc gtaacaactc cgccccacgc      540
gtgctagccc gggctcgaga tctgcgatct gcatctcaat tagtcagcaa ccatagtccc      600
gcccctaact ccgcccatcc cgcccctaac tccgcccac gcgt                       644
```

<210> SEQ ID NO 3
<211> LENGTH: 26
<212> TYPE: DNA
<213> ORGANISM: Artificial sequence
<220> FEATURE:
<223> OTHER INFORMATION: primer

<400> SEQUENCE: 3
ccgctcgaga ccttatgtac gtgcca                                          26

<210> SEQ ID NO 4
<211> LENGTH: 28
<212> TYPE: DNA
<213> ORGANISM: Artificial sequence
<220> FEATURE:
<223> OTHER INFORMATION: primer

<400> SEQUENCE: 4
ccgctcgagc tccaatggaa ctttcctg                                        28

<210> SEQ ID NO 5
<211> LENGTH: 28
<212> TYPE: DNA
<213> ORGANISM: Artificial sequence
<220> FEATURE:
<223> OTHER INFORMATION: primer

<400> SEQUENCE: 5
ccgctcgaga ctttcctgtt gattcacc                                        28

<210> SEQ ID NO 6
<211> LENGTH: 28
<212> TYPE: DNA
<213> ORGANISM: Artificial sequence
<220> FEATURE:
<223> OTHER INFORMATION: primer

<400> SEQUENCE: 6
ccgctcgagc aaaacccagt ggaaagtc                                        28

<210> SEQ ID NO 7
<211> LENGTH: 29
<212> TYPE: DNA
<213> ORGANISM: Artificial sequence
<220> FEATURE:
<223> OTHER INFORMATION: primer

<400> SEQUENCE: 7
ccgctcgaga tgccatatga gtgtattag                                       29

<210> SEQ ID NO 8
<211> LENGTH: 24
<212> TYPE: DNA
<213> ORGANISM: Artificial sequence
<220> FEATURE:
<223> OTHER INFORMATION: primer

<400> SEQUENCE: 8
cggaattcga tatccgcggc tctc                                            24

<210> SEQ ID NO 9
<211> LENGTH: 199
<212> TYPE: DNA
<213> ORGANISM: Artificial sequence
<220> FEATURE:
<223> OTHER INFORMATION: murine cytomegalovirus immediate early (mCMV
      IE) enhancer short version (IE2 enhancer short version)

<400> SEQUENCE: 9
tatgaatcag cacggtcatg cactctaatg gcggcccata gggactttcc acatagggggg    60 cgttcaccat ttcccagcat aggggtggtg actcaatggc ctttacccaa gtacattggg    120
tcaatgggag gtaagccaat gggttttttcc cattactggc aagcacactg agtcaaatgg   180

```
gactttccac tgggttttg                                                199
```

<210> SEQ ID NO 10
<211> LENGTH: 399
<212> TYPE: DNA
<213> ORGANISM: Artificial sequence
<220> FEATURE:
<223> OTHER INFORMATION: murine cytomegalovirus immediate early (mCMV
      IE) enhancer long version (IE2 enhancer short version)

<400> SEQUENCE: 10

```
tatgaatcag cacggtcatg cactctaatg gcggcccata gggactttcc acataggggg    60
cgttcaccat ttcccagcat aggggtggtg actcaatggc ctttacccaa gtacattggg   120
tcaatgggag gtaagccaat gggtttttcc cattactggc aagcacactg agtcaaatgg   180
gactttccac tgggttttgc ccaagtacat tgggtcaatg ggaggtgagc caatgggaaa   240
aacccattgc tgccaagtac actgactcaa tagggacttt ccaatgggtt tttccattgt   300
tggcaagcat ataaggtcaa tgtgggtgag tcaataggga ctttccattg tattctgccc   360
agtacataag gtcaataggg ggtgaatcaa caggaaagt                          399
```